United States Patent [19]

Rogers et al.

[11] Patent Number: 5,268,285
[45] Date of Patent: Dec. 7, 1993

[54] STRAINS OF YEAST WITH INCREASED RATES OF GLYCOLYSIS

[75] Inventors: David T. Rogers, Wayland; Jack W. Szostak, Boston, both of Mass.

[73] Assignee: Genetics Institute, Inc., Cambridge, Mass.

[21] Appl. No.: 733,472

[22] Filed: Jul. 22, 1991

Related U.S. Application Data

[63] Continuation-in-part of Ser. No. 533,992, Jun. 4, 1990, abandoned, which is a continuation of Ser. No. 85,099, Jul. 7, 1987, abandoned, which is a continuation-in-part of Ser. No. 796,551, Nov. 8, 1985, abandoned.

[51] Int. Cl.⁵ .................... C12N 15/63; C12N 1/19
[52] U.S. Cl. ...................... 435/172.3; 435/254.21; 435/194; 435/161; 435/320.1
[58] Field of Search .............. 435/161, 172.1, 194, 435/255, 256, 320.1, 172.3; 935/22, 28, 33, 37, 49, 66, 69

[56] References Cited

PUBLICATIONS

Sekikawa et al., "Defects in functional expression of an influenza virus hemogglutinin lacking the signal peptide sequences," PNAS, 80:3563–3567 (Jun. 1983).
Ke et al., "Molecular structure of fructose–1,6–bisphosphotase at 2.8-Å resolution," PNAS, 86:1475–1479 (Mar. 1989).
Foy et al., "Concentration of Metabolites and the Regulation of Phosphofructo-Kinases and Fructose-1,6-Bisphosphotase in *Saccharomyces cerevisiae*," Archives of Microbiology, 129(3):216–220 (1981).
Arima et al., "The nucleotide sequence of the yeast PHO5 gene: a putative precursor of repressible acid phosphotase contains a signal peptide," Nucleic Acids Research, 11(6):1657–1673 (1983).
Noda et al. "Characterization of Fructose 1,6–bisphosphatase from Bakers' Yeast" Journal of Biological Chemistry 259(11):7191–97 (Jun. 1984).
Mazon et al. "Inactivation of Yeast Fructose-1,6-bisphophatase" Journal of Biological Chemistry 257(3):1128–1130 (Feb. 1982).
McLeod et al. "Components of the Site-specific Recombination System encoded by the Yeast Plasmid 2-μ Circle," Cold Spring Harbor Symposia on Quantitative Biology 49:779–784 (1984).
Zoller et al. "Oligonucleotide-Directed Mutagenesis of DNA fragments cloned into M13 vectors" Methods in Enzymology 100:468–500 (1983).
Kingsman et al. "Heterologous Gene Expression in *S. cervisiae*" Biotechnology and Genetic Engineering Reviews 3:377–416 (Sep. 1985).
Albert L. Lehninger, "Biochemistry" 2nd Edition, pp. 235–236, 437–438, and 630–631, Worth Publishers, Inc. (New York, 1976).
Alessio Vassarotti et al., *The Journal of Biological Chemistry* 260(10):6348–6353 (1985).
John M. Sedivy et al., *J. Mol. Biol.* 186:307–319 (1985).
Rosine Haguenauer-Tsapis et al., *Molecular and Cellular Biology* 4(12):2668–2675 (1984).
Anthony H. Rose et al., "The Yeasts", Physiology and Biochemistry of Yeasts, vol. 2, pp. 274–275, ed. Academic Press, London and New York 1971).

*Primary Examiner*—Richard A. Schwartz
*Assistant Examiner*—James Ketter
*Attorney, Agent, or Firm*—Patricia A. McDaniels; Bruce M. Eisen; David L. Berstein

[57] ABSTRACT

The present invention provides a process for increasing the rate of production of carbon dioxide, ethanol and other fermentation products such as citric acid, produced by yeast such as *Saccharomyces cerevisiae* during fermentation, and decreasing biomass production by regulating the rate of glycolysis indirectly through changing the energy balance of the cell, i.e., by reducing intracellular ATP levels. Modifications for so altering the glycolysis rate involve the use of either a regulated ATP hydrolysis within the cell or a regulated leakage of ATP from the cell. This invention encompasses several ways for altering the yeast ATP level including (a) engaging futile metabolic cycles to increase ATP consumption; and (b) using an altered exocellular acid phosphatase so that it becomes intracellular to increase intracellular ATP hydrolysis; by which alterations in the ATP level may be turned off during growth of the yeast on a commercial scale, and then turned on before or during, and preferably before or at a very early stage of, the dough-rising phase.

11 Claims, 29 Drawing Sheets

GLUCOSE MEDIUM

GAL PROMOTER | FLP RECOMBINASE

RECOMBINATION SITE — HETEROLOGOUS GENE — RECOMBINATION SITE

FIG. 4A

GALACTOSE MEDIUM

GAL PROMOTER | FLP RECOMBINASE
EXPRESSION

RECOMBINATION

LOST

```
         10         20         30         40         50         60         70
ACCTGCTTAA GCAAATGCGC TTAAAAGCCG AACGCTCTAC CAACTGAGCT AACAAGGATG AGTTCTTCGA 80         90        100        110        120        130        140
ATTTTCCAGT CTAAGATAGA CAACCCATCA AACTGCATGG TCCCGGGCTA ACTTCTGCTC TCTTTTCCGG 150        160        170        180        190        200        210
ACGGATGGAA TCGCCCGCTTT TGAATTCACC TCCGGGGTAT TATTATTATT CTTAGTAGTC GCGGTCGTGC 220        230        240        250        260        270        280
GGACACCCGG AGTTATGCGG GCCCGAAAGC TCATTATGTA GTAAAGCTAG GTAATGTTAA GGGCGTAAGA 290        300        310        320        330        340        350
GCCAACGCAA GGCAGCAATA GCCTGGTATT CCCACACATC AAGAAAGCTT AAAAAGTTGA GACAGGGAAT 360        370        380        390        400        410        420
TTGAAGGCGA AGATTGCCGA ACTGGCCGA ACCCACTACT TTTTTTTTGG TTTGCTTGGT TTATTCCTGT 430        440        450        460        470        480        490
CGCTTGCCAA CTTGTGGCAT CTTCCCCACA CTATATTATA AGGATCGTCC TATGTATAGG CAATATTATC 500        510        520        530        540        550        560
CATTTCACTC GCTAACAAAT GTACGTATAT ATATGGAGCA ACAAGTAGTG CAATTACAGA CGTGTATTTT 570        580        590        600        610        620        630
GTCTTGATCT TGCTTTTTGT ATGATAGGCC TAAGAATAAC AGTGCGAACA TATAAGAAAC ATCCCTCATA
```

FIG. 8A/2

```
640                    656                        671                        686
CTACCACACA T ATG CCA ACT CTA GTA AAT GGA CCA AGA AGA GAC TCT ACC GAA GGG
          MET Pro Thr Leu Val Asn Gly Pro Arg Arg Asp Ser Thr Glu Gly 701                        716                        731
TTT GAT ACC GAT ATC ATC ACT CTT CCT AGA TTC ATA ATC GAG CAC CAG AAG CAA
Phe Asp Thr Asp Ile Ile Thr Leu Pro Arg Phe Ile Ile Glu His Gln Lys Gln 746                        761                        776                        791
TTT AAG AAC GCT ACT GGT GAT TTC ACA TTA GTA CTG AAT GCC TTG CAA TTC GCG
Phe Lys Asn Ala Thr Gly Asp Phe Thr Leu Val Leu Asn Ala Leu Gln Phe Ala 806                        821                        836
TTC AAA TTT GTA TCT CAC ACC ATC AGA CGT GCT GAA TTG GTT AAC TTG GTT GGG
Phe Lys Phe Val Ser His Thr Ile Arg Arg Ala Glu Leu Val Asn Leu Val Gly
```

FIG. 8B

```
851         866                 881                 896
TTA GCA GGC GCT TCC AAC TTC ACT GGT GAC CAG CAA AAG AAG TTG GAC GTT CTA
Leu Ala Gly Ala Ser Asn Phe Thr Gly Asp Gln Gln Lys Lys Leu Asp Val Leu 911                 926                 941                 956
GGT GAT GAA ATA TTT ATC AAT GCC ATG AGG GCT AGT GGG ATC ATC AAG GTC CTT
Gly Asp Glu Ile Phe Ile Asn Ala MET Arg Ala Ser Gly Ile Ile Lys Val Leu 971                 986                 1001
GTA TCT GAA GAA CAG GAA GAC TTG ATC GTT TTT CCC ACA AAC ACG GGC TCA TAC
Val Ser Glu Glu Gln Glu Asp Leu Ile Val Phe Pro Thr Asn Thr Gly Ser Tyr 1016                1031                1046                1061
GCA GTG TGT TGT GAT CCT ATT GAT GGC TCC AAT TTG GAC GCC GGT GTC TCC
Ala Val Cys Cys Asp Pro Ile Asp Gly Ser Asn Leu Asp Ala Gly Val Ser 1076                1091                1106
GTT GGA ACT ATC GCG TCT ATA TTC AGA CTG CTA CCA GAC TCA GGT ACT ATA
Val Gly Thr Ile Ala Ser Ile Phe Arg Leu Leu Pro Asp Ser Gly Thr Ile 1121                1136                1151                1166
AAC GAC GTA CTG AGA TGT GGT AAA GAA ATG GCC GCT TGC TAT GCC ATG TAC
Asn Asp Val Leu Arg Cys Gly Lys Glu MET Ala Ala Cys Tyr Ala MET Tyr 1181                1196                1211                1226
GGA TCC TCT ACG CAT CTA GTA TTG ACA TTG GTA GGA GTT GAT GGG TTT ACC
Gly Ser Ser Thr His Leu Val Leu Thr Leu Gly Asp Val Asp Gly Phe Thr 1241                1256                1271
TTA GAC ACA AAC TTG GGC GAA TTC ATC TTG ACT CAT CCT AAC TTA AGA ATT CCG
Leu Asp Thr Asn Leu Gly Glu Phe Ile Leu Thr His Pro Asn Leu Arg Ile Pro
```

FIG. 8B/2

```
      1286                  1301                  1316                  1331
CCT CAA AAG GCC ATC TAC TCA ATT AAT GAA GGT AAC ACC CTC TAC TGG AAC GAG
Pro Gln Lys Ala Ile Tyr Ser Ile Asn Glu Gly Asn Thr Leu Tyr Trp Asn Glu 1346                  1361                  1376
ACT ATA AGA ACA TTT ATT GAG AAA GTC AAA CAA CCC CAA GCA GAC AAC AAC AAC
Thr Ile Arg Thr Phe Ile Glu Lys Val Lys Gln Pro Gln Ala Asp Asn Asn Asn 1391                  1406                  1421                  1436
AAG CCT TTC TCG GCT AGG TAT GTT GGA TCC ATG GTT GCT GAT GTT CAC AGG ACG
Lys Pro Phe Ser Ala Arg Tyr Val Gly Ser MET Val Ala Asp Val His Arg Thr 1451                  1466                  1481                  1496
TTT CTT TAC GGT GGC CTT TTC GCA TAC CCT TGC GAC AAG AAG AGC CCC AAC GGA
Phe Leu Tyr Gly Gly Leu Phe Ala Tyr Pro Cys Asp Lys Lys Ser Pro Asn Gly 1511                  1526                  1541
AAA CTG AGG TTG CTT TAT GAG GCC TTC CCA ATG GCT TTC TTA ATG GAA CAA GCA
Lys Leu Arg Leu Leu Tyr Glu Ala Phe Pro MET Ala Phe Leu MET Glu Gln Ala
```

FIG. 8C

```
            1556                      1571                       1586                      1601
            GGG GGA AAA GCG GTC AAC GAT CGC GGA GAG AGA ATC TTG GAT TTG GTG CCA AGT
            Gly Gly Lys Ala Val Asn Asp Arg Gly Glu Arg Ile Leu Asp Leu Val Pro Ser
                      1616                      1631                      1646
            CAT ATC CAT GAC AAA TCT TCT ATT TGG TTG GGT TCT TCA GGT GAA ATT GAC AAA
            His Ile His Asp Lys Ser Ser Ile Trp Leu Gly Ser Ser Gly Glu Ile Asp Lys
            1661                      1676                      1695       1705       1715       1725
            TTT TTA GAC CAT ATT GGC AAG TCA CAG TAGTTCAATG ATCGCCTTCT TTTCTTATTT TCTTTGTTCT
            Phe Leu Asp His Ile Gly Lys Ser Gln
                 1735       1745       1755       1765       1775       1785       1795
            GTACTTTAGT ACGCGAAAAA AAAAAATCTG TATATGTCCT TATATATATA TATATTTATA TATATATATG
                 1805       1815       1825       1835       1845       1855       1865
            TGTATGTATG TGTACCGTAA GCATTACTCC TTCTAATAAT GAAAATTCTT AGGAAAAGAG AAAGGAAGTA
                 1875       1885       1895       1905       1915       1925       1935
            GCGAATGGAA TGGGATGGAA GTTTTAAAGA ACATTAGAAT TTATCCTTTG TCAAACTTCA TCACATCAAC
                 1945       1955       1965       1975       1985       1995       2005
            CAAGAACTAT ATAAACCTAC CAAATGAATT AAGAAACCTA ATTAGTGAAG AGCAGGAGAG TAAACTAGGG
                 2015       2025       2035       2045       2055       2065       2075
            TTCTTGCACA TCATTGAAAG TGATTTTAAA CCTTCGGTAG CGCTGCAAAA GTTGGTGAAT TGTACTACGG
                 2085       2095       2105       2115       2125       2135       2145
            GGGACGAAAA GATCCTAATC ATAGATATAG TATCAATATG GTCCCAACAA AAGCAAAGAC AGCATGGCGC
                 2155       2165       2175       2185       2195
            GATCTACACA AATTCGCTAT CTTGCATAAA CATCACGGGA TTAATCGTAT TTCTAGA
```

FIG. 9A yeast fdp

```
          10                      20
Met Pro Thr Leu Val Asn Gly Pro Arg Arg Asp Ser Thr Glu Gly Phe Asp Thr Asp Ile
          30                      40
Ile Thr Leu Pro Arg Phe Ile Ile Glu His Gln Lys Gln Phe Lys Asn Ala Thr Gly Asp
          50                      60
Phe Thr Leu Val Leu Leu Asn Ala Leu Gln Phe Ala Phe Lys Phe Val Ser His Thr Ile
          70                      80
Arg Arg Ala Glu Leu Val Asn Leu Val Gly Leu Ala Gly Ala Ser Asn Phe Thr Gly Asp
          90                     100
Gln Gln Lys Lys Leu Asp Val Leu Gly Asp Glu Ile Phe Ile Asn Ala Met Arg Ala Ser
         110                     120
Gly Ile Ile Lys Val Leu Val Ser Glu Gln Glu Asp Leu Ile Val Phe Pro Thr Asn
         130                     140
Thr Gln Ser Tyr Ala Val Cys Cys Asp Pro Ile Asp Gly Ser Ser Asn Leu Asp Ala Gly
         150                     160
Val Ser Val Gly Thr Ile Ala Ser Ile Phe Arg Leu Leu Pro Asp Ser Ser Gly Thr Ile
         170                     180
Asn Asp Val Leu Arg Cys Gly Lys Glu Met Val Ala Ala Cys Tyr Ala Met Tyr Gly Ser
         190                     200
Ser Thr His Leu Val Leu Thr Leu Gly Asp Gly Val Asp Gly Phe Thr Leu Asp Thr Asn
```

FIG. 9A/2

```
                                                    210                                 220
Leu Gly Glu Phe Ile Leu Thr His Pro Asn Leu Arg Ile Pro Pro Gln Lys Ala Ile Tyr
                                                    230                                 240
Ser Ile Asn Glu Gly Asn Thr Leu Tyr Trp Asn Glu Thr Ile Arg Thr Phe Ile Glu Lys
                                                    250                                 260
Val Lys Gln Pro Gln Ala Asp Asn Asn Lys Pro Phe Ser Ala Arg Tyr Val Gly Ser
                                                    270                                 280
Met Val Ala Asp Val His Arg Thr Phe Val Tyr Gly Leu Phe Ala Tyr Pro Cys Asp
                                                    290                                 300
Lys Lys Ser Pro Asn Gly Lys Leu Arg Leu Leu Tyr Glu Ala Phe Pro Met Ala Phe Leu
                                                    310                                 320
Met Glu Gln Ala Gly Gly Lys Ala Val Asn Asp Arg Gly Glu Arg Ile Leu Asp Leu Val
                                                    330                                 340
Pro Ser His Ile His Asp Lys Ser Ser Ile Trp Leu Gly Ser Ser Gly Glu Ile Asp Lys

Phe Leu Asp His Ile Gly Lys Ser Gln
```

FIG. 9B pig fdp

```
                                                                    10                                          20
Thr Asp Gln Ala Ala Phe Asp Thr Asn Ile Val Thr Leu Thr Arg Phe Val Met Glu Gln
                                                                    30                                          40
Gly Arg Lys Ala Arg Gly Thr Gly Glu Met Thr Gln Leu Leu Asn Ser Leu Cys Thr Ala
                                                                    50                                          60
Val Lys Ala Ile Ser Thr Ala Val Arg Lys Ala Gly Ile Ala His Leu Tyr Gly Ile Ala
                                                                    70                                          80
Gly Ser Thr Asn Val Thr Gly Asp Gln Val Lys Lys Leu Asp Val Leu Ser Asn Asp Leu
                                                                    90                                         100
Val Ile Asn Val Leu Lys Ser Ser Phe Ala Thr Cys Val Leu Val Thr Glu Glu Asp Lys
                                                                   110                                         120
Asn Ala Ile Ile Val Glu Pro Glu Lys Arg Gly Lys Tyr Val Val Cys Phe Asp Pro Leu
                                                                   130                                         140
Asp Gly Ser Ser Asn Ile Asp Cys Leu Val Ser Ile Gly Thr Ile Phe Gly Ile Tyr Arg
                                                                   150                                         160
Lys Asn Ser Thr Asp Glu Pro Ser Glu Lys Asp Ala Leu Gln Pro Glu Arg Asn Leu Val
                                                                   170                                         180
Ala Ala Gly Tyr Ala Leu Tyr Gly Ser Ala Thr Met Leu Val Leu Ala Met Val Asn Gly
                                                                   190                                         200
Val Asn Cys Phe Met Leu Asp Pro Ala Ile Gly Glu Phe Ile Leu Val Asp Arg Asn Val
```

FIG. 9B/2

```
                                                    210                                    220
Lys Ile Lys Lys Lys Gly Ser Ile Tyr Ser Ile Asn Glu Gly Tyr Ala Lys Glu Phe Asp
                                                    230                                    240
Pro Ala Ile Thr Glu Tyr Ile Glu Arg Lys Lys Phe Pro Pro Asp Asn Ser Ala Pro Tyr
                                                    250                                    260
Gly Ala Arg Tyr Val Gly Ser Met Val Ala Asp Val His Arg Thr Leu Val Tyr Gly Gly
                                                    270                                    280
Ile Phe Met Tyr Pro Ala Asn Lys Lys Ser Pro Lys Gly Lys Leu Arg Leu Leu Tyr Glu
                                                    290                                    300
Cys Asn Pro Met Ala Tyr Val Met Glu Lys Ala Gly Gly Leu Ala Thr Thr Gly Lys Glu
                                                    310                                    320
Ala Val Leu Asp Ile Val Pro Thr Asp Ile His Gln Arg Ala Pro Ile Ile Leu Gly Ser
                                                    330
Pro Glu Asp Val Thr Glu Leu Leu Glu Ile Tyr Gln Lys His Ala
```

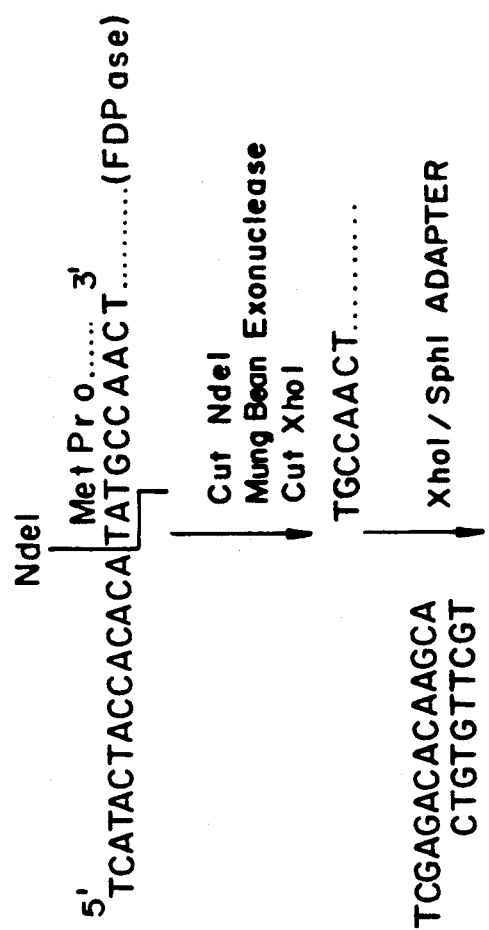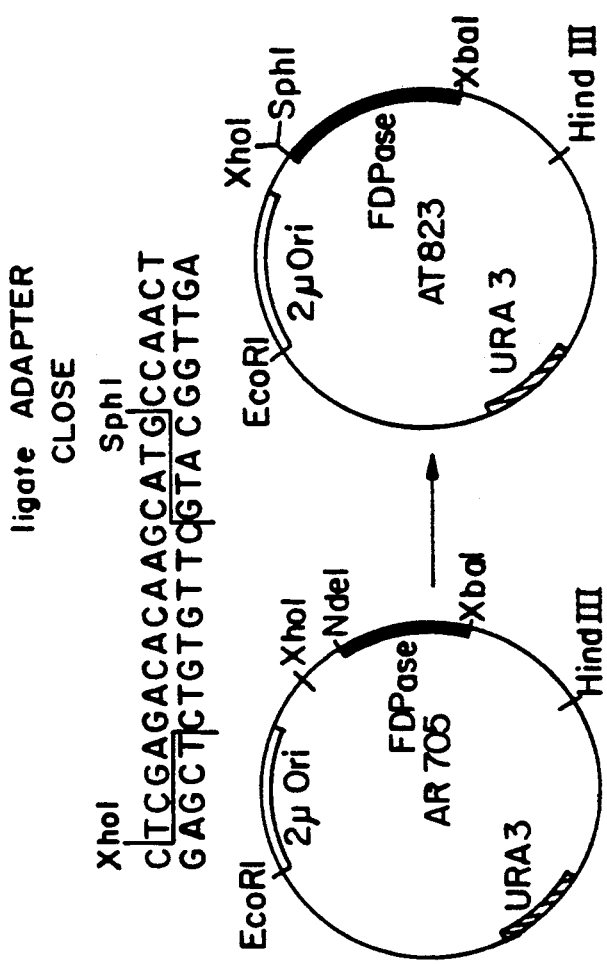
FIG. 10

FIG. 19

GGATCCGAAAGTTGTATTCAACAAGAATGCGCAAATATGTCAACGTATTTGGAAGTCAAC

TTATGTGCGCTGCTTTAATGTTTTCTCATGTAAGCGGACGTCGTCTATAAACTTCAA

ACGAAGCTAAAAGGTTCATAGCGCTTTTTTCTTTGTCTGCACAAAGAAATATATATTAAA

TTAGCACGTTTTCGCATAGAACGCAACGAACGCAACTGCACAATGCCAAAAAAAGTAAAA

```
                                              CLA1
                                               ↓
GTGATTAAAAGAGTTAATTGAATAGGCAATCTCTAAATGTATCGATACAACCTTGGCACT
```

CACACGTGGGACTAGCACAGACTAAATTTATGATTCTGGTCCCTGTTTTCGAAGAG

ATCGCACATGCCAAATTATCAAATTGGTCACCTTACTTGGCAAGGCATATACCCATTTGG

GAATAAAGGGTAAACACTTTGAATTGTCGAAATGAAACGTATATAAGCGCTGATGTTTTG

CTAAGTCGAGGTTAGTATGGCTTCATCTCTCATGAGAATAAGAACAACAAGAAATAGAGC

```
                 MetPheLysSerValValTyr.........
                  |  |  |  |  |  |  |
AAGCAAATTCGAGATTACCAATGTTTAAATCTGTTGTTTATTCAATTTTAGCCGCTTCT
```

```
           Kpn1
            ↓
TTGGCCAATGCAGGTACC
```

STRAINS OF YEAST WITH INCREASED RATES OF GLYCOLYSIS

This application is a continuation-in-part of U.S patent application Ser. No. 07/533,992, filed Jun. 4, 1990, now abandoned, which is a continuation of U.S. patent application Ser. No. 07/085,099, filed Jul. 7, 1987, now abandoned, which was a continuation-in-part of U.S. patent application Ser. No. 06/796,551, filed Nov. 8, 1985, now abandoned.

FIELD OF THE INVENTION

This invention relates to yeast, especially bakers or brewers yeast having higher rates of carbon dioxide and ethanol production This invention also relates to a novel means for regulating gene expression involving the regulated removal of a transcriptional block.

BACKGROUND OF THE INVENTION

Among the various recognized yeast genera, Saccharomyces is of the greatest economic and practical importance, as it is used extensively in the baking, brewing and winemaking industries, as well as in the production of biomass.

The major, although not the only, function of yeast in fermentation is to provide a source of carbon dioxide and ethanol. Sufficient yeast must be added to dough, wort or other fermentable substrate to obtain the desired rate of carbon dioxide and ethanol production. If a more active yeast were available, less yeast could be used, at a corresponding savings in cost.

Improving the fermentative power of yeast is an ongoing research effort. Both the dried yeast and the moist yeast forms may be improved to increase their carbon dioxide producing ability so as to (1) reduce fermentation time and/or (2) enable the use of less yeast, a considerable cost factor in baking as well as brewing. Improvements in yeast fermentative power also makes the preparation of the more stable active dry yeast (ADY) form attractive Generally, upon preparation of the ADY from a fresh yeast culture, about 40% of the fermentative ability is lost. Methods for eliminating or reducing this problem are continuously being sought.

One approach to improve dried yeast activity involves a modification of either the drying process, or the drying properties of the yeast strain, so as to prevent the loss of activity which occurs during drying. Process improvements have been made, and classical genetic approaches have been applied to this problem, with moderate success. See for example, U.S. Pat. No. 3,993,783.

Another approach to solving the problem of low activity dry yeast is described in U.S. Pat. No. 4,420,563. Yeast having improved leavening activity, particularly in sweet doughs of high sugar content, was produced by the incremental addition of salts to the growing yeast culture during the latter propagative stages The present invention is directed to genetic modifications which increase the carbon dioxide and ethanol producing activity of any yeast strain.

SUMMARY OF THE INVENTION

Disclosed herein are processes for increasing the rate of production of carbon dioxide, ethanol, and other fermentation products (e.g., citric acid) produced by yeast. In one aspect of the invention the ATP level of the yeast cell is reduced by substituting in the yeast genotype (e.g., via a single copy of multicopy vector or via cointegration into the yeast genome) a regulatable promoter for the natural promoter of a gene encoding a metabolic enzyme, for example, fructose-1, 6-diphosphatase, thus permitting the regulatable expression of the enzyme, thereby permitting the metabolic reaction catalyzed by the enzyme to proceed at the same time as the reverse reaction such that ATP is consumed, for example, by allowing expression of fructose-1, 6-diphosphatase during growth on glucose.

In another aspect of the invention, a gene encoding a metabolic enzyme, under the expression control of a promoter permitting constitutive expression of the gene is inserted into the yeast genotype thereby permitting the metabolic reaction catalyzed by the enzyme to proceed at the same time as the reverse reaction such that ATP is consumed. Further embodiments of this invention involve modifying the gene encoding the metabolic enzyme, e.g., to prevent or eliminate allosteric or other inhibition or inactivation of the enzyme.

In one embodiment, the enzyme FDPase gene may be mutagenized such that the codon for Ser-12 of the enzyme is replaced with a codon for an amino acid other than serine or such that allosteric inhibition, e.g., by AMP and/or fructose-2, 6-diphosphate, is reduced or eliminated In another embodiment, the genetic modification involves modifying a gene for an exocellular APase, e.g., by removing that portion of the gene encoding the leader sequence, such that the modified enzyme remains within the yeast cytoplasm and catalyzes the hydrolysis of intracellular ATP.

This invention further encompasses genetically modified yeast produced by the methods disclosed herein.

BRIEF DESCRIPTION OF THE DRAWINGS

FIGS. 4A and 4B illustrate the loss of a heterologous gene by regulated site specific recombination.

FIGS. 8A, 8B and 8C set forth the nucleotide sequence of the cloned yeast FDPase gene.

FIGS. 9A and 9B set forth the deduced amino acid sequence of the cloned FDPase enzyme and the amino acid sequence of pig FDPase, respectively.

FIG. 10 illustrates the construction of a FDPase cassette for expression from a heterologous promoter.

FIG. 19 illustrates the DNA sequence for the yeast acid phosphatase promoter and the beginning of the structural gene for acid phosphate (PHO 5).

DETAILED DESCRIPTION OF THE INVENTION

Figure 1:
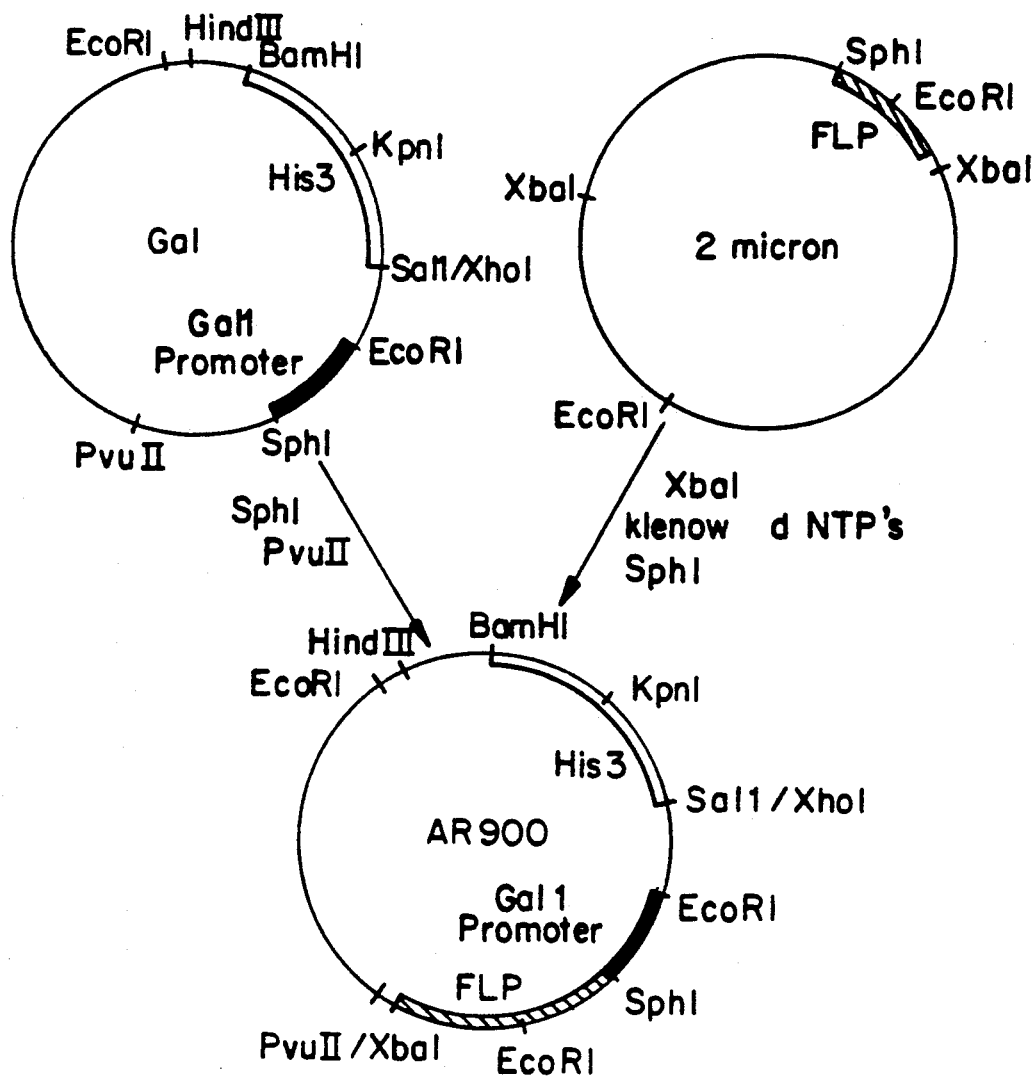
FIG. 1 illustrates the construction of an integrating yeast plasmid containing the FLP gene expressed from the Gall promoter

Generally, the processes, vectors and yeast of the present invention reduce the level of ATP in the yeast cell, thereby stimulating glycolysis This may be accomplished by inducing ATP-consuming futile cycles or by introducing cytoplasmic acid phosphatase activity One advantage provided by this invention is that the genetic modifications may be "turned on" only during, and preferably at the early stage of, the leavening phase and not during the production-level growth of the yeast Alternatively, the genetic modifications may be constitutively expressed such that they are turned on during large scale production, i.e., commercial scale growth of the yeast, for the enhanced production of fermentation products such as ethanol.

Regulation of the genetic modifications may be achieved by using a temperature sensitive promoter or a promoter which is induced by the presence of a specific substance such that the enzyme is expressed only at a predetermined temperature or in the presence of the substance. Alternatively, expression control may be provided by inserting into the yeast genome a FLP gene construct described in greater detail herein.

Vectors useful in these processes include single copy, centromere containing plasmids and multicopy plasmids containing the yeast 2u origin of replication, as well as vectors permitting the cointegration thereof into the yeast genome.

(i) ATP-consuming Futile Cycles

One genetic modification for reducing cellular ATP levels is the use of a normal metabolic pathway in an abnormal manner to consume ATP, so that glycolysis is stimulated. Most preferably, the chosen pathway is cyclic, so that its abnormal use results in no significant net accumulation or depletion of any required metabolic intermediate, substrate or product. Many metabolic pathways in yeast are capable of running in opposite directions depending on the growth conditions or requirements of the cell. For example, metabolite "A" may be converted into metabolite "B", or "B" into "A", as required by the cell. Causing such a pathway to run in both directions at the same time results in no net accumulation or loss of metabolites but does, however, consume the energy required to run the pathways, and in this respect is a "futile" cycle. Of course, other futile cycles involving additional steps can also be used (e.g., A→B→C→A). Transcriptional, translational and post-translational controls can be used to turn on or off such a futile cycle, where, for every revolution of the cycle, one molecule of ATP is consumed without producing any net accumulation of the product or loss of substrate In bakers yeast, the metabolic change necessary to reduce ATP levels and thereby stimulate glycolysis is preferably regulated so that it is operable only during leavening A preferred futile cycle for consuming ATP is: fructose-6-phosphate →fructose-1, 6-diphosphate →fructose-6-phosphate. The enzymes involved in this pathway, phosphofructokinase and fructose 1, 6-diphosphatase (FDPase or FBPase) have been extensively characterized (Bloxham and Lardy, *The Enzymes*, Vol. 8, Boyer, Ph.D., Ed., pp 239-278 (1973); Uyeda, *Adv. Enzymology* 48:193-244 (1979); Foy and Bhattachargee, *Arch. Microbiol.* 129:215-220 (1981); Funayama et al (1979)). By cloning the gene for FDPase and exchanging its promoter for one which is regulated, the gene is expressed at will. We have found that expressing this gene during growth on glucose is sufficient to accomplish a considerable loss of ATP and a consequent increase in the rate of glycolysis Optimizing the FDPase-driven futile cycle requires understanding the natural regulation of FDPase.

Natural FDPase Regulation

In order to prevent futile cycling between the synthesis and hydrolysis of fructose-1, 6-diphosphate in wild type yeast, this enzyme is rapidly inactivated when glucose is added to cells growing on non-fermentable carbon sources This inactivation of FDPase appears to occur in three stages. An initial inhibition of enzyme activity is accomplished by allosteric regulation (Lenz and Holzer, *F.E.B.S. Letter* 109:271-274 (1980); Wolf and Holzer, *Transport and Utilization of Aminoacids, Peptides and Proteins by Microorganisms*, Payne, J.W., Ed., John Wiley, Chinchester, 1980; Tortora et. al., *Biochem. Biophys. Res. Comm.* 100:688-695 (1981)). When glucose is added to yeast cells, the concentration of fructose-2, 6-diphosphate rises within seconds from undetectable levels to concentrations of several uM, enough to partially inhibit FDPase. The mechanisms that regulate the synthesis of fructose-2, 6-diphosphate are unclear (Gancedo et al., *J. Biol. Chem.* 258: 5998-5999 (1983)). After the initial rapid inhibition, a second step involving phosphorylation of the FDPase occurs over a period of several minutes (Muller and Holzer, *Biochem Biophys. Res. Comm.* 107:1482-1489 (1982)). The state of phosphorylation of FDPase is controlled by a specific kinase and a specific phosphatase The phosphorylation occurs at a particular serine residue (Muller and Holzer supra; Mazon et al., *J. Biol. Chem.* 257: 1128-1130 (1982)). The modified FDPase is less active than the unmodified enzyme. Finally, the phosphorylated enzyme appears to be a substrate for a specific protease which catalyzes an irreversible inactivation of the FDPase, over a period of about an hour.

Genetic Modifications for Regulating FDPase

There are several genetic approaches that block the natural inactivation of FDPase. Mutants which do not synthesize fructose-2, 6-diphosphate, or which have an FDPase that does not bind the inhibitor, block the inactivation cascade at the beginning Site specific mutagenesis of the serine that otherwise becomes phosphorylated yields an enzyme resistant to the second and third steps. Some enzyme activity remains after the initial partial inhibition by fructose-2, 6-diphosphate (Lenz and Holzer, supra: Wolf and Holzer, supra; Tortora et al., supra). This enzyme activity is enough to cause significant futile cycling We have identified the site of phosphorylation ($Ser_{12}$) in FDPase and have altered it by conventional site specific mutagenesis (Zoller and Smith, supra.). We have found that an amino acid substitution for the serine to prevent phosphorylation is sufficient to produce enough enzyme activity to cause a significant level of futile cycling. The serine may also be changed to another amino acid such as threonine, valine, or cysteine.

However, the enzyme is also inhibited by high concentrations of AMP (Taketa and Pogell, *J. Biol Chem* 240:651–662 (1965)). For further optimization the enzyme (which is already somewhat resistant to AMP inhibition by virtue of the substitution at $Ser_{12}$) may additionally be altered at its AMP binding site to overcome this inhibition. The binding site of AMP on the enzyme has been characterized. To achieve enhanced enzymatic activity for the futile cycle this site may be mutated in vitro and reintroduced into yeast and the loss of inhibition by AMP indirectly assayed. On plates a mutant form of the enzyme no longer inhibited by AMP allows the yeast to grow normally on a gluconeogenic carbon source but very poorly on glucose, thus permitting a convenient assay for such a modification.

Since the enzymes involved in this futile cycle are fairly major yeast proteins, this pathway is sufficient to consume a considerable amount of ATP. The stimulation of glycolysis is "fine tuned" to give any desired level of carbon dioxide output by changing the copy number of the altered fructose diphosphatase gene, the strength of the promoter or the promoter used in the FDPase or FDPase-variant expression vector as described In addition to the previously described modifications, this invention further contemplates alteration of the allosteric regulation of FDPase by fructose 2, 6-diphosphate or AMP.

Fructose-2, 6-phosphate is synthesized via an enzymatic pathway from fructose-6-phosphate by the enzyme fructose-6-phosphate-2-kinase (Clifton and Fraenkel, *J. Biol. Chem.* 258:9245 (1983) and Pilkis et al., *J. Biol. Chem.* 259:949 (1949)).

One method for reducing inhibition of enzyme activity is to mutate the cloned copy of FDPase in vitro (See e.g., Shortle et al., *Proc. Natl. Acad. Sci.* 79:1588 (1982)) and introduce it back into the cell on a self-replicating selectable yeast plasmid followed by assaying for the loss of the inhibitory effects of fructose 2, 6-diphosphate and AMP. In principal, the loss of a site where an allosteric inhibitor binds is often a fairly conservative change in the enzyme structure since even a slight modification of the binding site is expected to greatly alter its affinity for fructose-2, 6-diphosphate. This approach requires a good assay for the altered enzyme. Since FDPase is under the control of an inducible promoter, when the futile cycle is working efficiently, under inducing conditions, mutant colonies growing on a fermentable carbon source are very small but under non-inducing condition the colonies are normal in size. The suspected mutant colonies are also plated on a gluconeogenic carbon source where they grow normally under inducing conditions. Such colony screening methods may therefore be used to assay for the altered enzyme.

Finally, the altered FDPase is introduced into the strain of yeast used for baking by the procedures described above. Bakers yeast containing the altered FDPase are found to have substantially increased leavening ability

Alternative Futile Cycles

There are a surprisingly large number of alternative futile cycles which could be engaged to consume ATP. For example, the conversion of phosphoenolpyruvate to pyruvate by pyruvate kinase can be reversed (Katz, J. and Rognstad, R., *Cur. Top. Cell. Reg.* 10:237–289 (1976) and Reeves, R. E., *Biochem. J.* 125:531 (1971)). Alternatively many other futile cycles will waste ATP including those found in amino acid biosynthesis and degradation, polyphosphate synthesis and degradation, fatty acid biosynthesis and pyrimidine biosynthesis. Since all are strictly controlled at the transcriptional level, a futile cycle may be induced by changing the regulation of the enzymes involved by changing their promoters. However, such cycles have additional regulatory mechanisms. Generally, the additional regulation involves feedback inhibition or allosteric modulation of enzyme function by intermediates or energy metabolites. If desired, such allosteric binding sites may be modified to eliminate or reduce allosteric inhibition in analogous fashion to the methods described herein in the illustrative case of FDPase. Other classes of regulation involve the sequestering of one of the enzymes in an organelle, where substrate availability can be controlled, or in the trapping of unstable intermediates in an enzyme complex, allowing them to be quickly converted to a stable intermediate. All of these pathways are potential inducible ATP hydrolysing processes and may therefore be used to consume ATP via appropriate genetic modification.

(ii) Introduction of Enhanced Cytoplasmic Acid Phosphatase Activity

An alternative modification for regulating the rate of glycolysis involves producing a cytoplasmic acid phosphatase to hydrolyze organic phosphates including ATP. The normally exocellular acid phosphatase of the yeast *Saccharomyces cerevisiae* is an inducible non-specific phosphatase located in the periplasm. The gene for this enzyme has been recently cloned and characterized. (See Rogers et al., *Proc. Natl. Acad. Sci., U.S.A.* 79:2157–2161 (1982)). Preventing the phosphatase from being secreted into the periplasm of the cell (e.g., by genetic modification removing the enzyme's secretory leader) will result in dephosphorylating organic phosphates in the cytoplasm, including ATP. However, this non-specific phosphatase will also dephosphorylate other important organic phosphates causing serious damage to the metabolism of the cell. The level of "trapped" cytoplasmic phosphatase must therefore be strictly controlled. For example it was found that the natural promoter for yeast acid phosphatase (PHO5) expresses too much ATPase activity when fully induced to achieve an increase in the rate of glycolysis. To have a regulated method of hydrolysing ATP by a cytoplasmic acid phosphatase, a weaker promoter is preferably used such that is have the desired effect when fully induced or the basal level of an inducible promoter can be used as illustrated below. This can be accomplished in several ways, examples of which are described below.

Regulated Promoters

Numerous promoters useful in yeast transformation vectors are known in the art which may be used in the practice of this invention. As discussed in greater detail herein, regulated promoters, many of which are known in the art, are preferred in certain embodiments of this invention. Examples of regulated yeast promoters are those from genes in galactose, maltose, phosphate or nitrogen metabolism, isocytochromes and alcohol dehydrogenase II.

A specific example of a regulated promoter is that from the yeast acid phosphatase gene (PHO5). The promoter reportedly acts in response to levels of inorganic phosphate in the media. It is possible that a strong promoter such as that from acid phosphatase (APase) may yield a higher than optimal expression level for certain embodiments of this invention, e.g., futile cycling The desired regulated promoter can be modulated in several ways. For example, a cloned copy of the acid phosphatase promoter can be mutated in vitro using the method of Shortle (Shortle et al., *Proc. Natl Acad. Sci. USA* 79:1588 (1982)) or small deletion/substitutions within the promoter can be generated by insertion of linkers by known techniques (McKnight and Kingsbury, *Science* 217:316 (1982), Heffron and McCarthy, *Proc. Natl. Acad. Sci. USA* 75:6012 (1978)). A pool of DNA fragments containing the mutated acid phosphatase promoter is inserted into a yeast/*E. Coli* shuttle plasmid where the promoter expresses a detectable marker, for example, the beta-galactosidase or beta-lactamase gene from *E. coli* (Guarente and Ptashne, *Proc. Natl. Acad. Sci. USA* 78:2199 (1981); Rose et al., *Proc. Natl Acad. Sci. USA* 78:2460 (1981); Martinez and Casadaban, *Mol. Cell. Biol.* 3:580 (1983); and Silverman et al., *Mol. Cell. Biol.* 2:1212 (1982)). Transformed yeast colonies are then screened for the production of the detectable marker, e.g., on media containing 5-bromo-4-chloro-3-indolyl-beta-D-Galactoside (X-gal) where the desired phenotype gives white colonies on high phosphate media and light blue colonies on low phosphate media. Both strong and weak promoters may thus be identified. DNA is obtained from the yeast cells showing a suitable phenotype and transformed into *E. Coli* using standard techniques Ampicillin resistant colonies must contain the yeast plasmid. Plasmid DNA is made from these *E. Coli* transformants and the acid phosphatase promoter from the plasmids used for expression.

Alternatively, a temperature sensitive regulatory gene may be used. For example, many mutants in the pho R and pho U regulatory genes of the acid phosphatase pathway are found to give constitutive expression at 36° C. and normal regulation at 23° C. (Ueda et al., *J. Bact.* 122:911 (1975)). The plasmid of interest containing the PHO5 promoter is transformed into a yeast strain containing a pho R or pho U temperature sensitive mutation and the acid phosphatase promoter is regulated by changing the culture temperature in a high phosphate containing medium. This mode of regulation is also used in conjunction with a weak (mutated) acid phosphatase promoter Another method for regulating the modifications of this invention to use another regulated promoter which is naturally much weaker than the acid phosphatase promoter. Several such promoters have been identified. One example is the promoter from the yeast HO gene. The expression of this promoter is controlled indirectly by mutations in the Sir locus (Rine, "Regulation and Transposition of Cryptic Mating type genes in *Saccharomyces cerevisiae*", Ph.D. thesis, University of Oregon at Eugene (1979)). In a normal "wild type" cell which was Mat a at the Mating type locus, an alpha cassette HML and the HO allele at the homothallic locus, the HO promoter would be turned on. If the strain carries a Sir mutation however both Mat a and Mat alpha (from HML) are expressed and the HO promoter would be turned off. Therefore a strain carrying a temperature sensitive Sir mutation may be used where the HO promoter is expressed at low temperature but repressed at high temperature.

The regulated promoter is turned "off" during growth of baker's yeast and "on" at the end of fermentation, or in the bread dough, by changing the yeast culture conditions For example, when using the APase promoter the yeast are grown in the presence of a regulated amount of phosphate so that the culture uses all of the phosphate before the end of fermentation. At this time, the APase promoter is induced by the depletion of phosphate from the fermenter. If a temperature sensitive expression system is used, the culture temperature is set such that the promoter is turned "off" during growth and "on" at the end of fermentation Where desired, the quantity of ATP consumed by the modified cell may be regulated to maximize $CO_2$ and ethanol production. This can be accomplished by using a stronger or weaker promoter or modulating its activity, or by using a temperature sensitive regulatory gene whose degree of regulation is dependent upon the temperature of the culture.

(iii) Regulated site specific recombination

One problem for optimizing the expression of an ATP reducing process in baking yeast is the difficulty in identifying a promoter which can be regulated so that it is turned off during growth of the yeast but on during leavening This is especially difficult since the yeast is used for many different types of baking applications where the consistency of the yeast may not be controllable due to different handling conditions which may affect the regulated promoter. If a promoter regulated by the same growth conditions as is normally required for production of $CO_2$, i.e., glycolysis, is used, the yeast should be as consistent as the standard baking yeast.

Unfortunately glycolytic genes are not strongly transcriptionally regulated nor are they continually suppressed during growth of the baking yeast However, triggering the expression of an ATP reducing process by a glycolytic promoter at the end of the growth fermentation would overcome these objections.

A novel approach was therefore devised which allows the yeast to grow up without wasting ATP, but have the ATP reducing process expressed from a glycolytic promoter during the leavening process. This is accomplished using a regulated, site specific recombination event to remove a transcriptional block within the promoter, for example the GPDH promoter, and is described in more detail below. It should be noted that this unusual expression strategy may be used for regulating the expression of a wide variety of genes, including, but not limited to, those encoding enzymes for futile cycling or cytoplasmic phosphatases.

Vectors

The gene responsible for inducing a futile cycle or the cytoplasmic acid phosphatase gene may be cloned under the transcriptional control of a promoter into two types of autonomously replicating expression vector: a single copy, centromere containing plasmid, or a multicopy plasmid Alternatively, the DNA may be introduced into the yeast chromosome by recombination. In addition, these vectors contained a selection gene and 3' noncoding regions, as are well known in the art.

The vectors are transformed into a strain of yeast and the yeast cells selected for those containing the vector by a selection protocol as is well known in the art. The selected yeast cells containing the vector, i.e., transformed cells, are grown in a suitable growth media and the promoter induced to start the loss of cytoplasmic ATP.

Suitable selection genes are well known in the art. It is preferred that the selection agent be one that prevents cell growth in the absence of the selection gene. Thus, cells that lose the plasmid in large scale culture do not contain the selection gene and will not over-grow during the fermentation However, it may be desirable in the commercial production of desired products to avoid the use of certain cell toxins, thereby simplifying the product purification steps. Thus, a desirable selection gene is one that enables transformants to grow in a media lacking a nutrient required for growth of the parental strain. Useful selection genes in the practice of this invention include for example, URA3, LEU2, etc.

The vectors useful herein can be synthesized by techniques well known to those skilled in the art. The components of the vectors such as selection genes, promoters, and the like can be obtained from natural sources or synthesized as discussed below. Basically, components which are available in large quantity (i.e., which are present on natural plasmids, e.g., the 2μ plasmid of yeast, or which can be readily synthesized) can be assembled with the appropriate use of restriction enzymes and T4 DNA ligase If a component is not available in large quantity, it can be amplified by insertion into a bacterial cloning vector such as a plasmid or phage as is well known in the art. Then, with appropriate use of restriction enzymes, large quantities of vector can be obtained by techniques well known in the art by simply culturing the bacteria, digesting its DNA with an appropriate endonuclease, separating the DNA fragments, identifying the DNA containing the component of interest and recovering same. Ordinarily, a transformation vector is assembled in small quantity and then ligated to a suitable autonomously replicating synthesis vector such as a plasmid or phage for production of larger amounts of transformation vector DNA. The well known pBR322 plasmid, for example, can be used in most cases.

The synthesis vectors are used to clone the ligated transformation vectors in conventional fashion, e.g., by transformation of a permissive prokaryotic organism, replication of the synthesis vector to high copy number, and recovery of the synthesis vector by cell lysis and separation of the synthesis vector can be directly transformed into yeast cells. Many different types of yeast vectors are readily available and may be substituted where appropriate (Parent et al., *Yeast* 1:83-138 (1985)).

Certain vectors including tranformation vectors and vectors containing various elements such as specific promoters, the FLP gene and an FDPase gene have been deposited on Nov. 5, 1986 in *E. coli* HB101 with the American Type Culture Collection, 12301 Parklawn, Drive, Rockville, MD 20852 (USA), including the following:

| | | |
|---|---|---|
| 1. AZ402 | plasmid contains URA3 transcriptional block flanked by FLP recognition sequences within a BglII/SalI cassette (ATCC No. 67257) | |
| 2. AU125 | Plasmid contains an FDPase gene operatively linked to the GPDH promoter (ATCC No. 67256) | |
| 3. AT823 | plasmid contains an FDPase gene (ATCC No. 67258) | |
| 4. AR900 | plasmid contains the FLP gene operatively linked to the GalI promoter with restriction sites for the substitution of other promoters for the GalI promoter; plasmid provides for regulated expression of the FLP gene (ATCC No. 67259) | |
| 5. YOpl | plasmid is an illustrative example of a selectable 2μ plasmid (ATCC No. 67260) | |
| 6. BA601 | plasmid contains mutagenized (ser-12 to ala) FDPase gene operatively linked to the GPDH promoter (ATCC No. 67261) | |
| 7. M138 | multicopy plasmid for expression of a cytoplasmic (mutagenized) APase gene (ATCC No. 67262) | |
| 8. N305 | similar to M138 except that the plasmid contains a yeast centromere and is therefore a single copy plasmid (ATCC No. 67263) | |

Genetic Modification of Baking and Brewing Strains

Baking and brewing yeast strains present a more difficult substrate for transformation than laboratory strains since they are polyploid and do not generally contain auxotrophic markers which can be used for the selection procedures which are well known in the art.

However a modified or a heterologous gene/promoter construct such as the FDPase gene linked to the GPDH promoter, discussed below, can be introduced into the strain of yeast used for baking by using dominant drug resistant genes such as the antifungal agents gentamicin (G418) (Jiminez and Davies, Nature 287:869 (1980)) or hygromycin B (Gritz and Davies, *Gene* 25:179-188 (1983)). As an example of this approach, a resistance gene coding for aminocyclitol phosphotransferase (ACPT) is carried by the bacterial transposon TN601 which confers resistance to G418, but its promoter is weak and therefore is only partially effective at conferring resistance. Jimenez and Davies, supra. The promoter is exchanged for a yeast promoter (e.g., the yeast glyceraldehyde phosphate dehydrogenase promoter).

A plasmid is then constructed containing the desired gene/promoter construct with its natural chromosomal flanking regions together with the TN601 ACPT described above. This plasmid does not contain a yeast origin of replication. The strain of bakers yeast is transformed with this plasmid and transformants selected on G418 plates. The plasmid copy of ACPT can only be stably maintained if the plasmid is integrated into the yeast genome at the natural gene locus This results in a tandem duplication of the gene (e.g., FDPase) separated by the plasmid and ACPT sequences Growth of these transformants in the absence of G418 allows for the loss of the plasmid by "looping out" leaving behind either the "wild type" or the introduced sequence. These G418 sensitive clones are then screened by Southern hybridization of genomic DNA using oligonucleotide probes for the presence of the heterologous construct using standard techniques.

EXPERIMENTAL EXAMPLES

Materials

All DNA restriction and metabolism enzymes were purchased from New England Biolabs. These enzymes were used in conditions and buffers described by New England Biolabs, except mung bean exonuclease which was obtained from PL Biochemicals and used as described. ATP and the deoxynucleoside triphosphate (dNTPs), i.e., dATP, dGTP, cCTP and dTTP, were purchased from PL Biochemicals and [$^{32}$P] was obtained from New England Nuclear Corporation.

Ligation reactions were carried out as described by Maniatis et al., *Molecular Cloning, A Laboratory Manual*, Cold Spring Harbor Laboratory, Cold Spring Harbor, N.Y. (1982), the disclosure of which is incorporated herein by reference, using the buffer described at page 246 thereof and using a DNA concentration of 1-100 μg/ml, at a temperature of 23° C. for blunt ended DNA and 16° C. for "sticky ended" DNA. Electrophoresis was done in 0.5-1.5% agarose gels containing 90 mM Tris-borate, 10 mM EDTA.

After DNA digestion restriction enzymes were inactivated by heating to 65° C. for 10 minutes When performing sequential reaction the DNA was precipitated with 70% ethanol after each step. After "filling in" a restriction site by reaction with the large fragment of DNA polymerase (Klenow) and the four dNTPs, the reaction mixture was made 10 μM magnesium chloride and an equal volume of 5M ammonium acetate was added. The DNA was precipitated with 2 volumes of ethanol at −20° and the DNA pelleted by centrifugation at 4° C. for 10 minutes in an Eppendorf microfuge. The ethanol was poured off and the pellet dissolved in 10μl/μg DNA of 0.2M sodium acetate. The DNA was re-precipitated with 2 volumes of ethanol and centrifuged as before The DNA pellet was dried under vacuum before proceeding to the next step in the construction Synthetic oligonucleotides were kinased as described in Maniatis et al., supra. and annealed by heating to 65° C. and slow cooling to 4° C. before use.

DNA preparation and transformation

Purification of "super coiled" plasmid DNA from *E. coli* and the transformation of *E. coli* was as described in Maniatis et al., 1982, supra. Transformation of yeast was as described by Hinnen et al., *Proc. Natl. Acad. Sci. USA* 75:1929-1933 (1978), except that 1.2M Sorbitol was used instead of 1.0M. Small scale plasmid preparation for screening transformed bacteria was essentially that described (Maniatis et al., 1982, supra; Holmes and Quigley, *Anal. Biochem.* 14:193 (1981)) except that the RNAse digestion was performed after the restriction enzyme digestion by adding 1 μl of a 1 mg/ml solution of RNAse (Boehringer Mannheim) to the well of the agarose gel just before electrophoresis.

Strains and Media

*E. coli* strain HB101 was used for all bacterial transformations. Yeast strains DB745 (Botstein et al., *Gene* 8:17-24 (1979)), KY114 or ATCC 26675 were used. *E. Coli* were grown in LB media with or without ampicillin (49 ug/ml) as described (Maniatis et al., 1982, supra.). Prior to transformation, yeast were grown at 30° C. in media containing 1% yeast extract (Difco), 1% Bacto Peptone (Difco) and 2% glucose. Yeast minimal media contained 5g ammonium sulfate, 10g glucose, 40 mg adenine, 60 mg leucine, 2μg inositol, 400 μl niaoin, 100 μg p-aminobenzoic acid, 400 μg pyridoxine hydrochloride, 500 μg boric acid, 40 μg copper sulphate, 100 μg potassium iodide, 200 μg sodium molybdate, 400 μg zinc sulfate, 500 mg magnesium sulphate, 100 mg sodium chloride, 100 mg calcium chloride and 1g (high phosphate media) or 10mg (low phosphate media) potassium phosphate (monobasic) per liter. For induction of the acid phosphatase promoter, cells were pregrown at 30° C. on high phosphate yeast minimal media, washed free of phosphate, and transferred to low phosphate yeast minimal media to resume growth at 30° C. Maximum induction occurred 8 to 12 hours after transfer The fermenter was run at 30° C. and an agitation setting of 4. Nitrogen was continuously bubbled through the vessel at a rate of 500 cc/min and the off gas passed through a moisture trap of Dry-Rite and into a Perkin Elmer Mass Spectrometer gas analyzer for the measurement of carbon dioxide.

In continuous culture, media was fed at a rate of 250 ml/hr using a Pharmacia model M3 pump. When carbon dioxide measurements were being taken, all settings, volumes and temperature were checked and adjusted if necessary. Media feed, temperature and agitation were found to be fairly stable, however, the nitrogen gas feed varied by as much as 10% over a four hour period. Therefore, the output from the gas analyzer was fed into a chart recorder and the rate of flow of nitrogen adjusted manually over a two hour period. The rate of flow of nitrogen and the level of carbon dioxide in the off gas was checked for stability over this period before taking measurements of cell density in the culture. The culture was therefore demonstrated to be stable within the limits of detection before measurements were taken. This was born out by the reproducibility of the data. Culture density was measured by dilution of the culture ten fold in water and reading the density in a Bausch and Lomb Model Spectronic 20 at 600 nm.

Vector Construction

Figure 7:
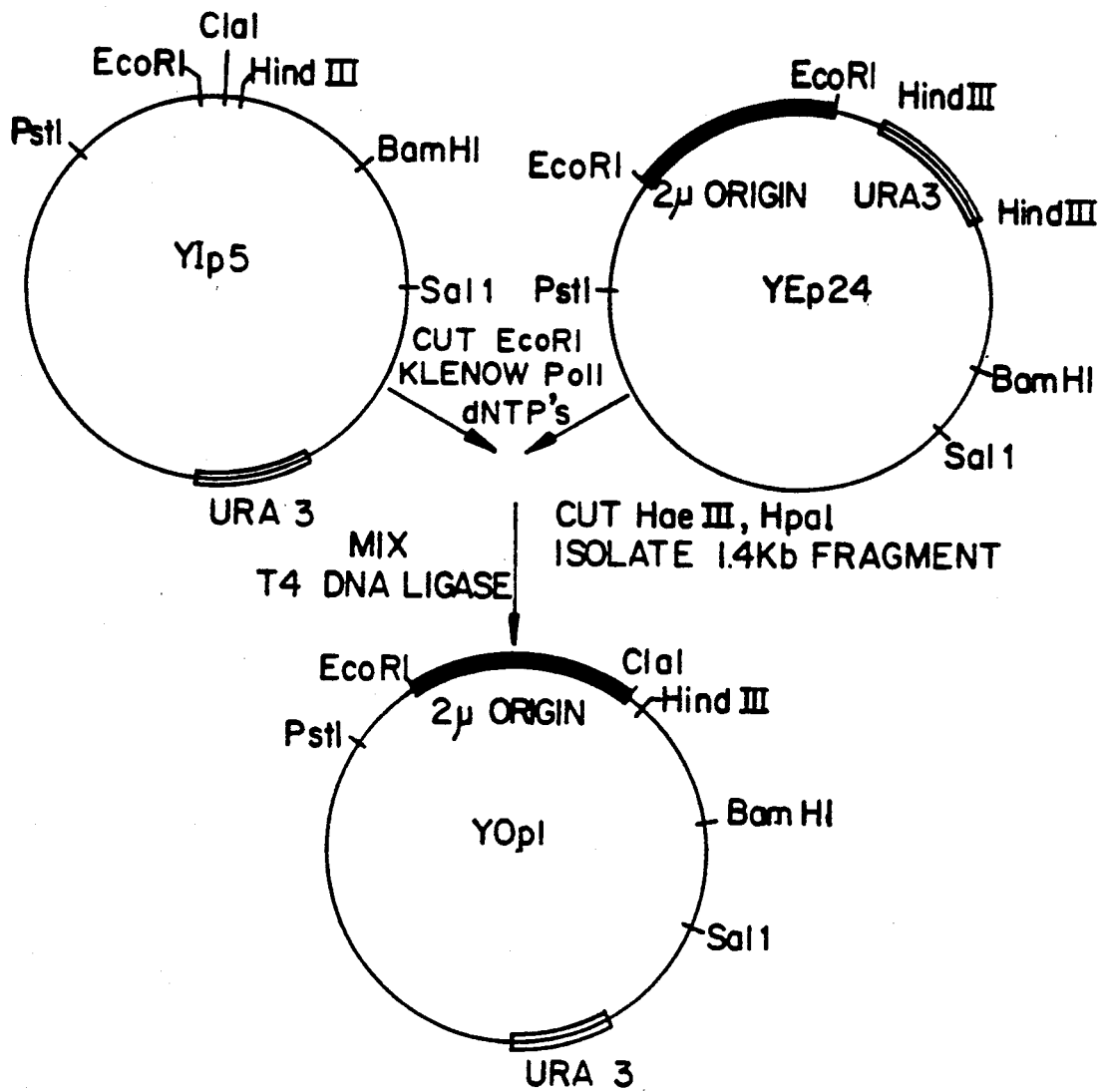
FIG. 7 illustrates the construction of an expression vector containing origins of replication, and selectable markers for both yeast and E. coli.
Figure 11:
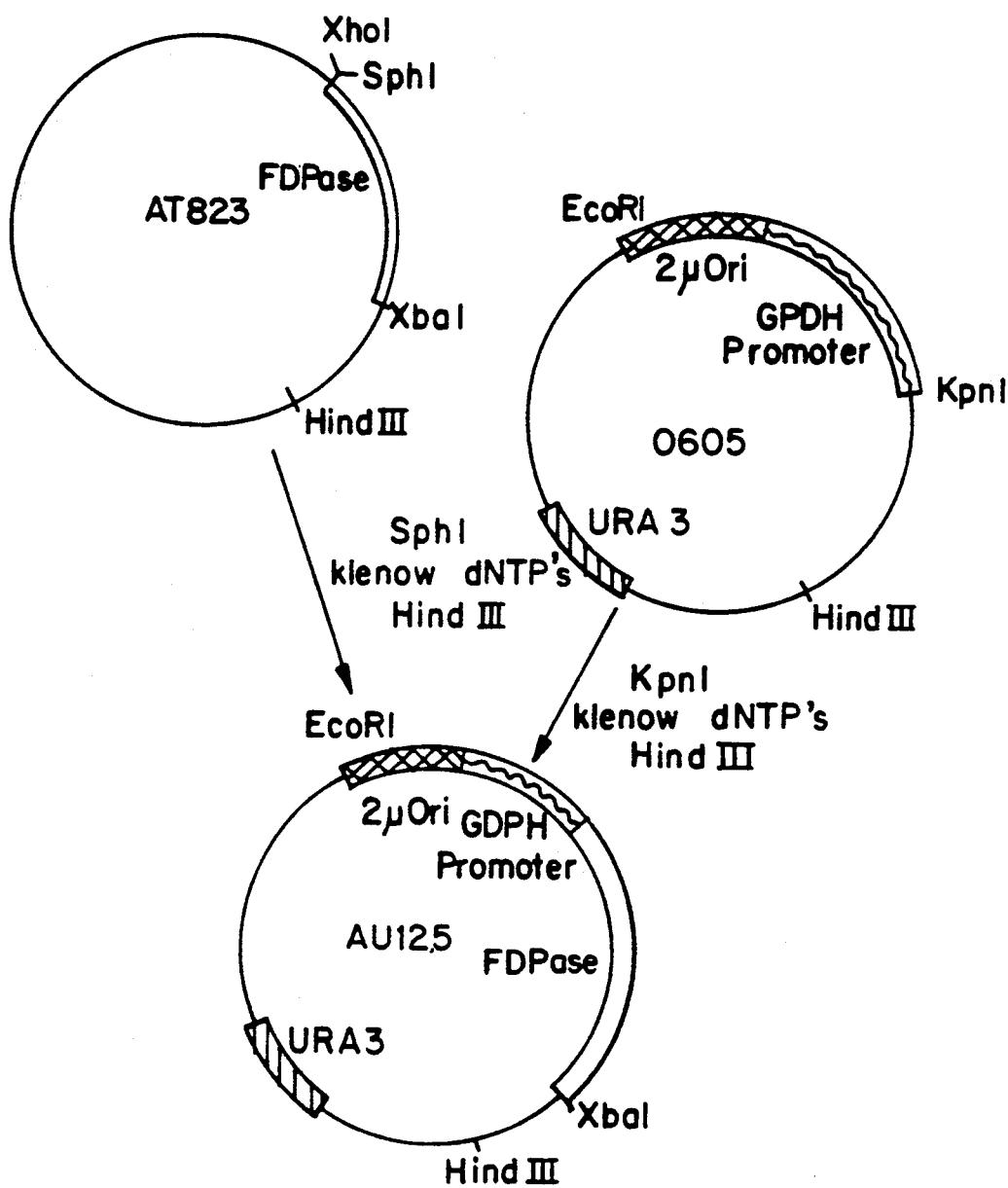
FIG. 11 illustrates the synthesis of an expression vector where FDPase is expressed from the GPDH promoter

To minimize the size of the expression plasmid and to reduce the number of restriction sites, a plasmid was constructed which contained the uracil 3 gene (URA3) as a selection gene and the 2μ origin of replication. Alternatively, another yeast plasmid could be used such as YEp24 or YEp13 or equivalent (Parent et al., supra.). Our plasmid was derived from YIp5 (Botstein et al., supra.) with the addition of a HaeIII/HpaI fragment, containing the origin of replication from the 2μ plasmid of yeast. The plasmid, YOp1 (FIG. 7), was constructed by introducing the 2μ origin into the EcoRI site of YIp5 Plasmid DNA from YEp24 (Botstein et al., supra.) was cut with restriction enzymes HaeIII and HpaI and the DNA run on a preparative 1.0% Agarose gel. The 1.4 kb fragment containing the 2μ origin of replication was identified by comparison with the migration pattern of molecular weight marker fragments and electroeluted into a well cut into the agarose. The DNA fragment was purified by passing the buffer from the well over a DEAE Sephacel column (Maniatis et al., supra.). Plasmid YIp5 was cut with EcoRI and the "sticky ends" "filled in" using the Klenow fragment of DNA polymerase I and all four dNTPs. The HaeIII/HpaI fragment from YEp24 was ligated into the "filled in" EcoRI site of YIp5 (FIG. 7). The ligation mixture was transformed into HB101 and the resulting ampicillin resistant colonies screened for the presence of the 2μ origin fragment Since "filled in" EcoRI site ligated to a HaeIII site re-creates the EcoRI site, the orientation of the fragment was determined by mapping the resulting EcoRI site to restriction sites on the plasmid. A plasmid (YOpl) having the EcoRI site proximal to the PstI site within the ampicillin resistant gene was used in subsequent constructions

EXAMPLE 1

Loss of ATP by futile cycling

Isolation for the Gene for Fructose 1,6-diphosphatase

The gene for FDPase was isolated by complementation of a deletion mutant of FDPase in *E. Coli* (strain DF657, CGSC number 6695). A plasmid library of "wild type" yeast genomic DNA in a pBR322 plasmid vector was transformed into DF657 by selection for antibiotic resistance and a plasmid carrying the yeast FDPase gene identified by its ability to allow the bacteria to grow on a gluconeogenic carbon source. The yeast FDPase clone was sequenced using the dideoxynucleotide sequencing method of Sanger et al., *Proc. Natl. Acad. Sci. USA* 74:5463-5467 (1977), (FIG. 8). Comparison of the amino acid sequence of yeast FDPase derived from the DNA sequence showed greater than 50% homology with the amino acid sequence of purified pig FDPase (Marcus et al (1982) *Proc. Natl. Acad. Sci. USA* 79:7161-7165) (FIG. 9) confirming the correct identification of the yeast clone.

Since a futile cycle must be carefully regulated to prevent premature wasteage of ATP, the first adaption of the natural FDPase gene was to change its promoter for that of a sequence which could be regulated during the fermentation. A restriction site analysis of the DNA sequences of yeast FDPase identified a NdeI site very close to the start of the coding region (FIG. 10). In vitro mutagenesis was used to adapt the 5' end of the clone for expression from a heterologous yeast promoter by converting the NdeI site to an SphI site The FDPase gene was first subcloned into pBR322 to create plasmid AR705, FIG. 10. Plasmid AR705 was digested with NdeI and treated with mung bean exonuclease An adapter containing four out of six base pairs of an SphI site at one end and a XhoI overhang at the other end was ligated to the plasmid, digested with XhoI and the plasmid closed using T4 DNA ligase to generate plasmid AT823, FIG. 10. The ligation mix was transformed into bacteria and ampicillin resistant colonies screened for the presence of the SphI and XhoI sites The FDPase gene in plasmid AT823 was ligated to the promoter from the gene for glyceraldehyde phosphate dehydrogenase (GAP491) [Holland and Holland (1980), J. Biol. Chem. 255:2596-2605] as follows. Plasmid O605 (FIG. 13), derived from plasmid M903, was digested with KpnI, treated with the Klenow fragment of DNA PolI, and cut with HindIII Plasmid AT823 was cut with SphI, treated with the Klenow fragment of DNA PolI, cut with HindIII, and the 3.8 kb SphI/HindIII fragment was isolated and ligated to the HindIII/KpnI-digested O605 to generate plasmid AU125. Expression of the FDPase gene in plasmid AU125 is now regulated by the GPDH promoter.

FDPase mutagenesis

The plasmid containing the FDPase with the heterologous promoter was transformed into yeast and transformants tested for expression of the FDPase clone. FDPase activity was detectable when cells were grown under inducing conditions on a gluconeogenic or glycolytic carbon source. When growing using fermentation, it would be expected that allosteric inhibitors and enzyme inactivation would reduce enzyme activity.

Since inactivation is mediated by phosphorylation of a serine residue, a change in the structural gene contemplated by this invention is the elimination of this phosphorylation site. The serine residue which is phosphorylated has been identified as residue 12 (the only cAMP dependent protein kinase recognition site in the sequence and from peptide mapping of purified phosphorylated enzyme and the amino acid sequencing of the phosphorylated peptide (Rittenhouse et al. (1986) *J. Biol. Chem.* 261:3939-3943)).

Figure 13:
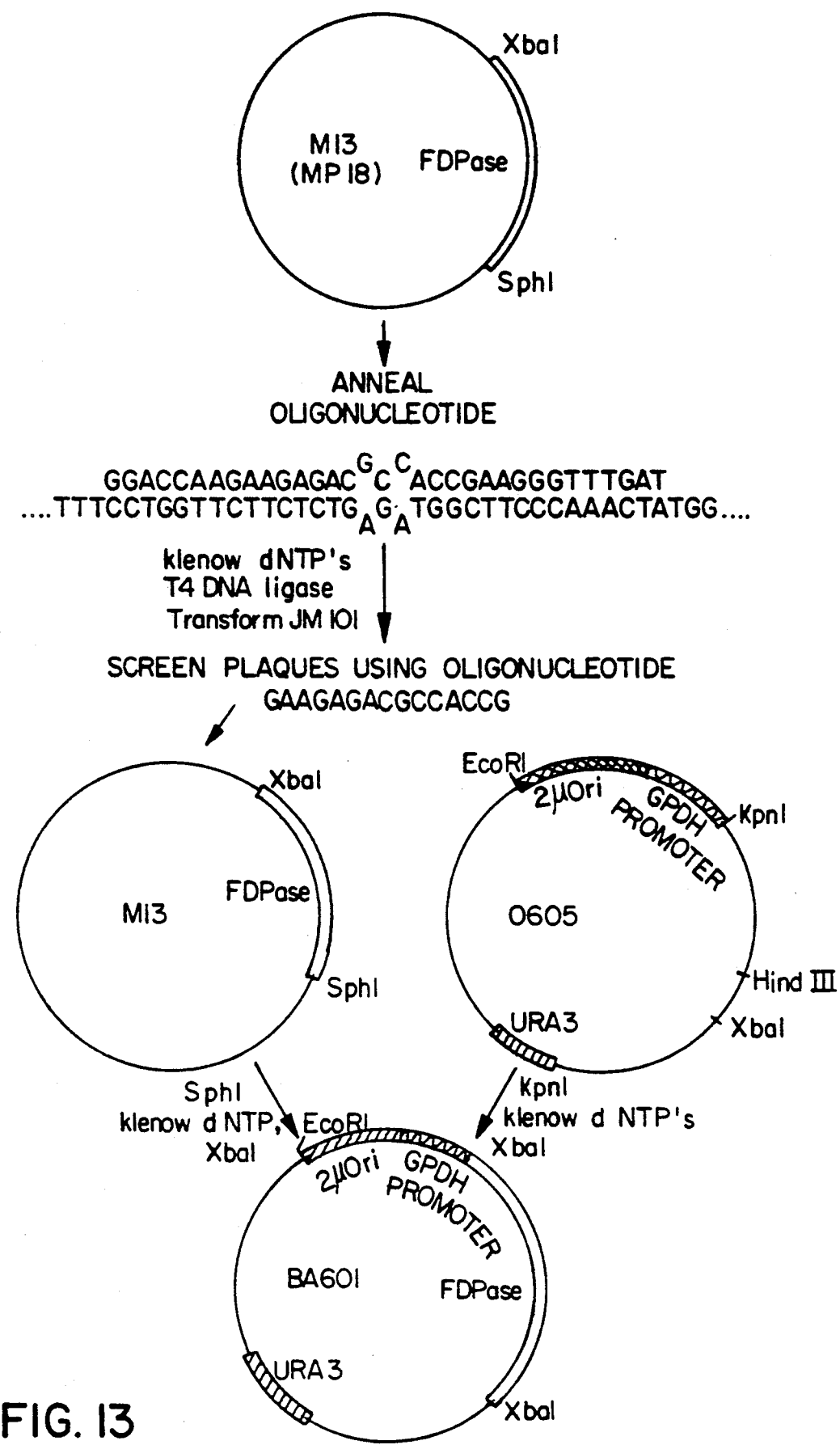
FIG. 13 illustrates the exchange of the serine residue at the protein kinase recognition site for an alanine.

Fructose 1, 6-diphosphatase (FDPase) serine (residue 12) was changed to an alanine using site directed mutagenesis (Zoller and Smith, supra.). This is a conservative change which would not be expected to affect the activity of the non-phosphorylated protein but would prevent phosphorylation of the enzyme. Such changes may be made using site directed mutagenesis (FIG. 13). This was achieved by cloning that part of the sequence around this residue into a single stranded DNA virus, M13. A synthetic oligonucleotide was made which hybridized to this region of the DNA but was a mismatch at the serine residue such that the sequence substitutes an alternate codon. A double stranded molecule was then made from this hybrid by the use of the Klenow fragment of DNA polymerase PolI. The reaction is conducted in the presence of all four deoxynucleotide triphosphates and DNA ligase. This hybrid double stranded DNA was then cloned into bacteria, replicated, re-isolated and re-transformed into bacteria to resolve the two strands. Half of the progeny contain the sequence for the serine, and half contain the substituted sequence for the alanine or other codon of choice. They were distinguished by hybridization to a short oligonucleotide (17 bp) complimentary to the substituted sequence. This substituted gene was then put back into the multicopy GPDH expression vector as described above and transformed into a laboratory strain of yeast, e.g., KY114.

In order to measure the rate of glycolysis, cultures of yeast expressing clones of FDPase from the glyceraldehyde phosphate dehydrogenase (GPDH) promoter were examined in small one liter fermentors. Cultures were grown in batch and nitrogen was bubbled through the culture at 110 ml/min. Carbon dioxide and cell density were measured periodically.

Figure 14B:
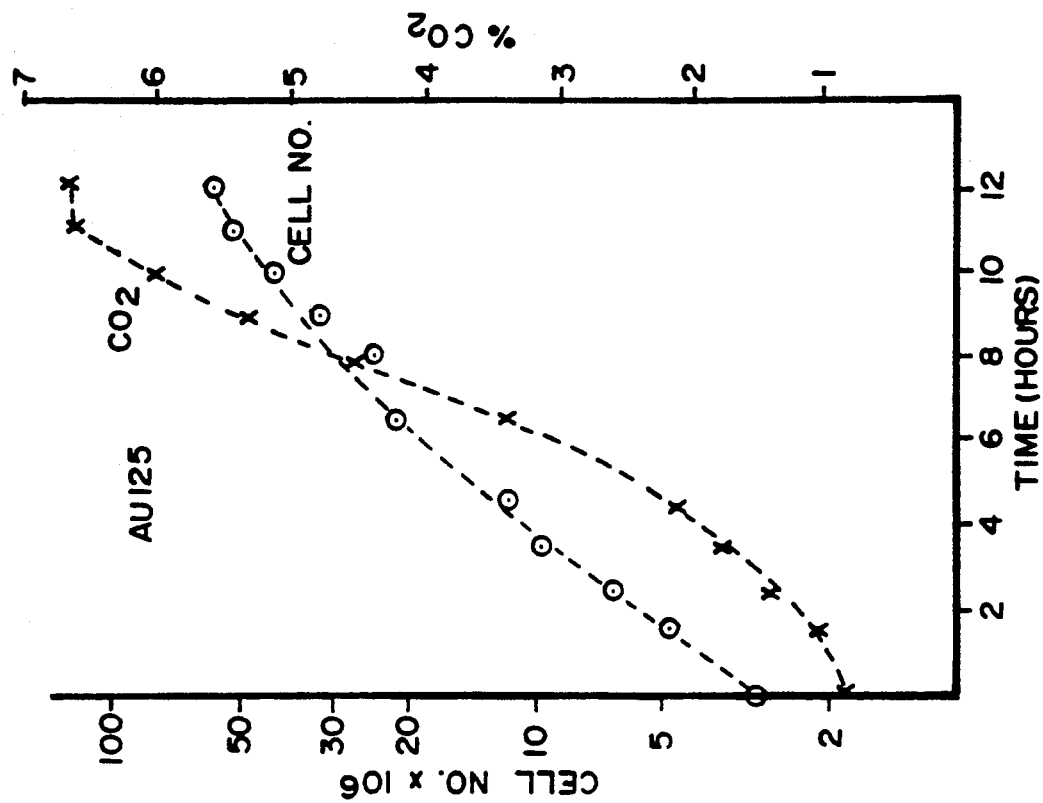
FIGS. 14A, 14B and 14C illustrate carbon dioxide evolution during fermentation of yeast cultures expressing wild type FDPase or amino terminally deleted FDPase.
Figure 14A:
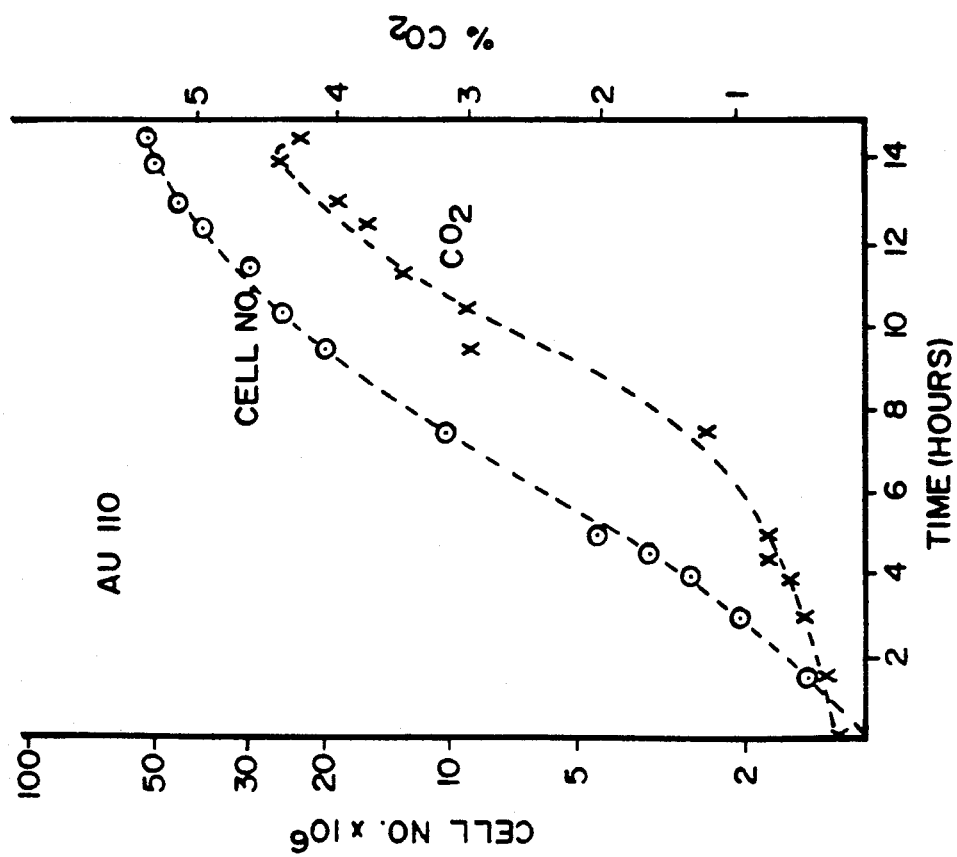
Figure 14C:
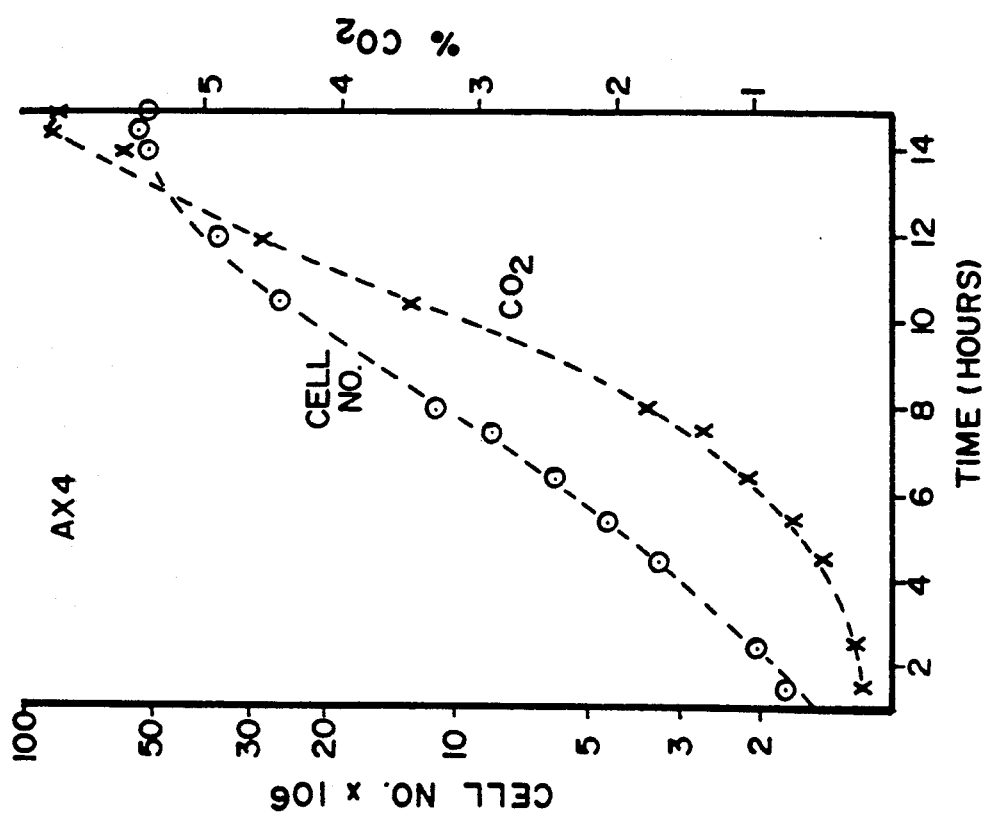

Initially, cultures of yeast expressing the wild type enzyme (plasmid AU125) was compared to a control plasmid containing a non-expressed FDPase (plasmid AU110) (FIG. 14). The level of carbon dioxide produced by the cultures at the beginning of the growth cycle is very similar However at the end of the growth cycle, substantially higher levels of $CO_2$ were produced in the strain expressing FDPase.

After specific point mutants in the phosphorylation site of FDPase had been created, fermentation experiments were repeated. In these experiments, strain ATCC 26675, expressing FDPase containing the serine to alanine mutation from the GPDH promoter (plasmid BA601) or a control plasmid where FDPase was not expressed (plasmid BA802) were tested. Strain ATCC 26675 has been found to give the highest level of inactivation of many yeast strains tested. These cultures should give a conservative estimate of the possible increase in gassing power.

Figure 15B:
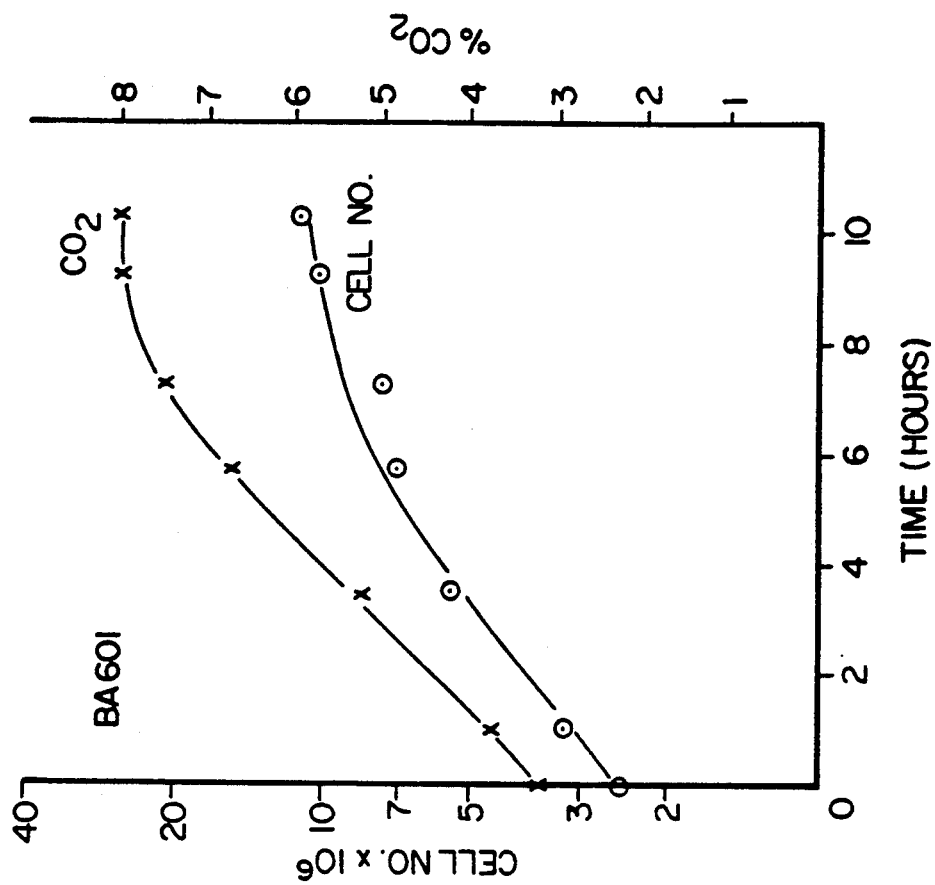
FIGS. 15A and 15B illustrate carbon dioxide evolution during fermentation of yeast cultures expressing FDPase lacking the recognition site for cyclic AMP dependent protein kinase
Figure 15A:
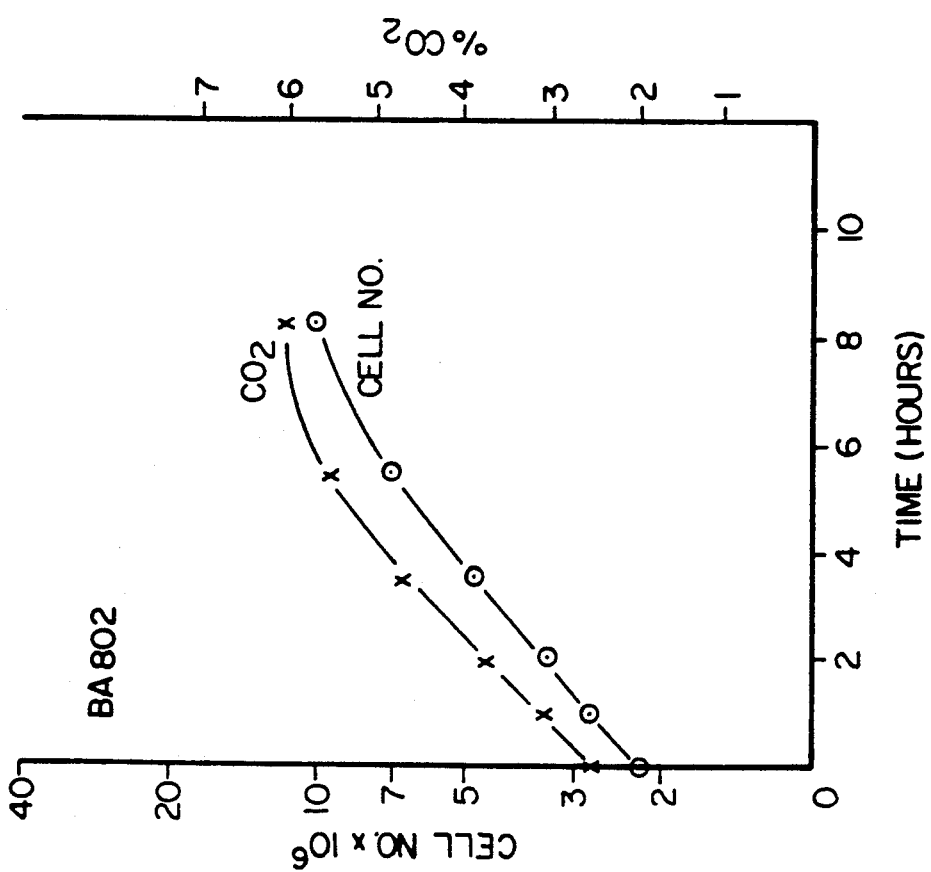

Fermentations were performed as before and carbon dioxide and cell density measured. Carbon dioxide output is again increased toward the end of the growth cycle in the strain expressing FDPase (FIG. 15). The fermentation experiment was repeated and gave good reproducibility. Cultures were harvested at the end of the growth cycle, centrifuged, and examined using a gassing test described below.

Figure 17:
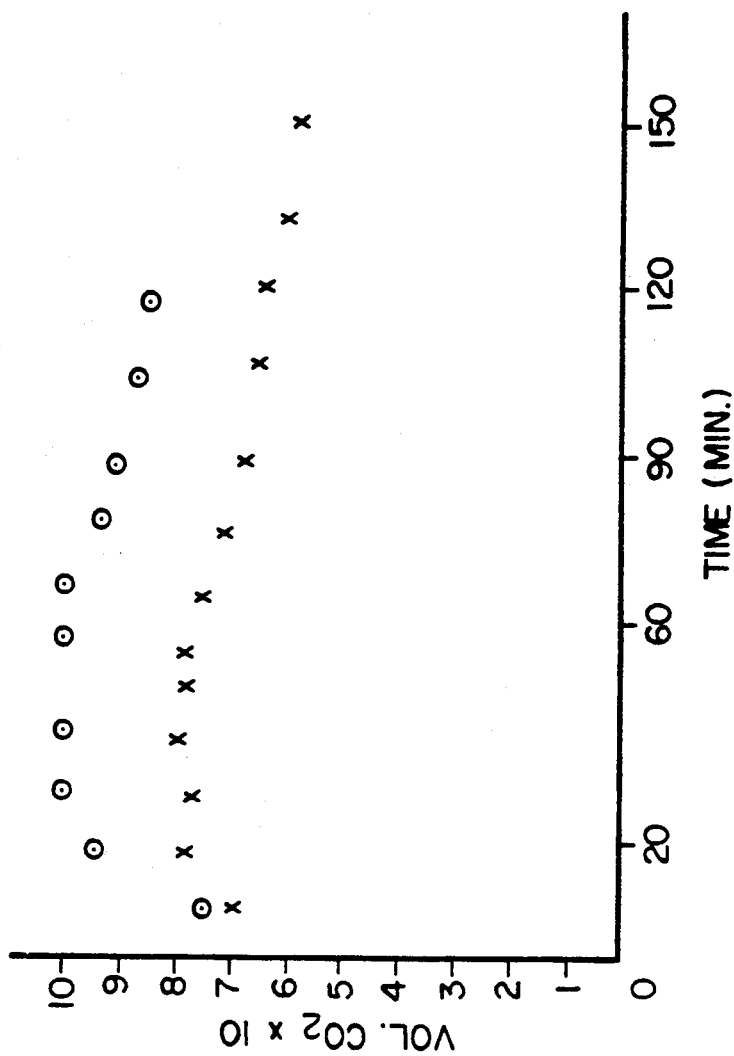
FIG. 17 illustrates the improvement in gassing power of a strain of yeast expressing the gene for the non-phosphorylated FDPase enzyme.
Figure 16:
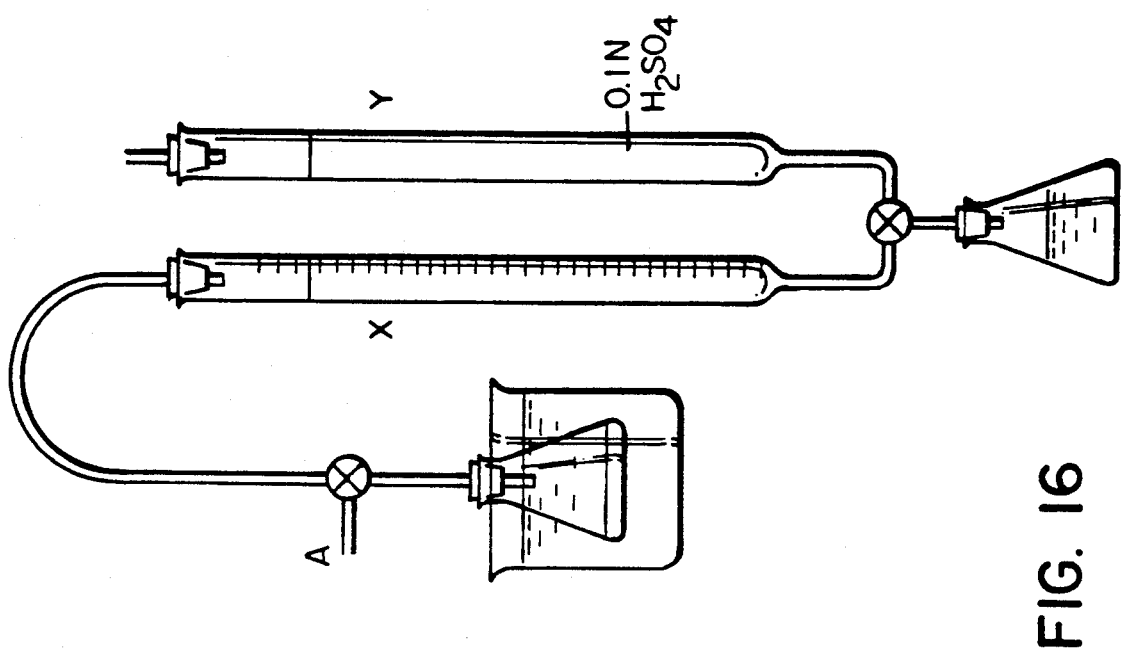
FIG. 16 illustrates the apparatus used in the gassing test.

Gassing tests were performed in an apparatus illustrated in FIG. 16. The flask contained one gram of cells, one gram of glucose and 10 ml of media (yeast nitrogen base, Difco) and had a final OD 600 nm of 12. All solutions were at 32° C. The water bath was also at 32° C. Tube a was open during the first 10 minutes after the flask was placed in the water bath. Measurements of $CO_2$ evolution were made periodically by closing tube a and measuring the amount of $CO_2$ evolved in burette X after adjusting the level of liquid in burette Y to that in burette X to bring the gas in burette X to atmospheric pressure. Measurements were taken until 100 ml of $CO_2$ had been produced. The rate of $CO_2$ production in the strain containing the plasmids described above are illustrated in FIG. 17. In this test the strains expressing the mutant FDPase gave an increase of 25% in gassing power.

EXAMPLE 2

Expression of a cytoplasmic acid phosphatase

Preparation of the Promoter Fragment of APase

Figure 3:
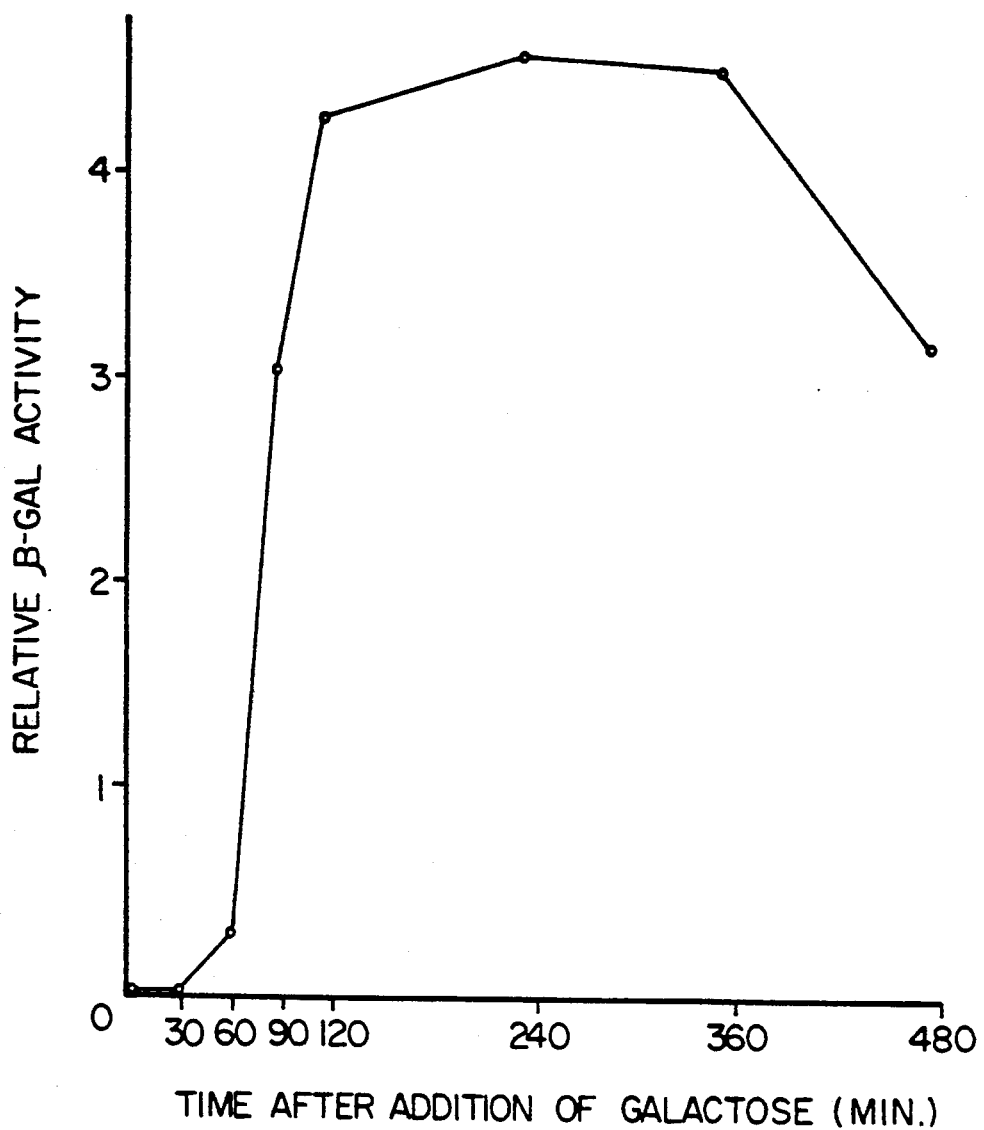
FIG. 3 illustrates the induction of $\beta$-galactosidase activity from the Gall promoter under glucose limited growth.
Figure 18:
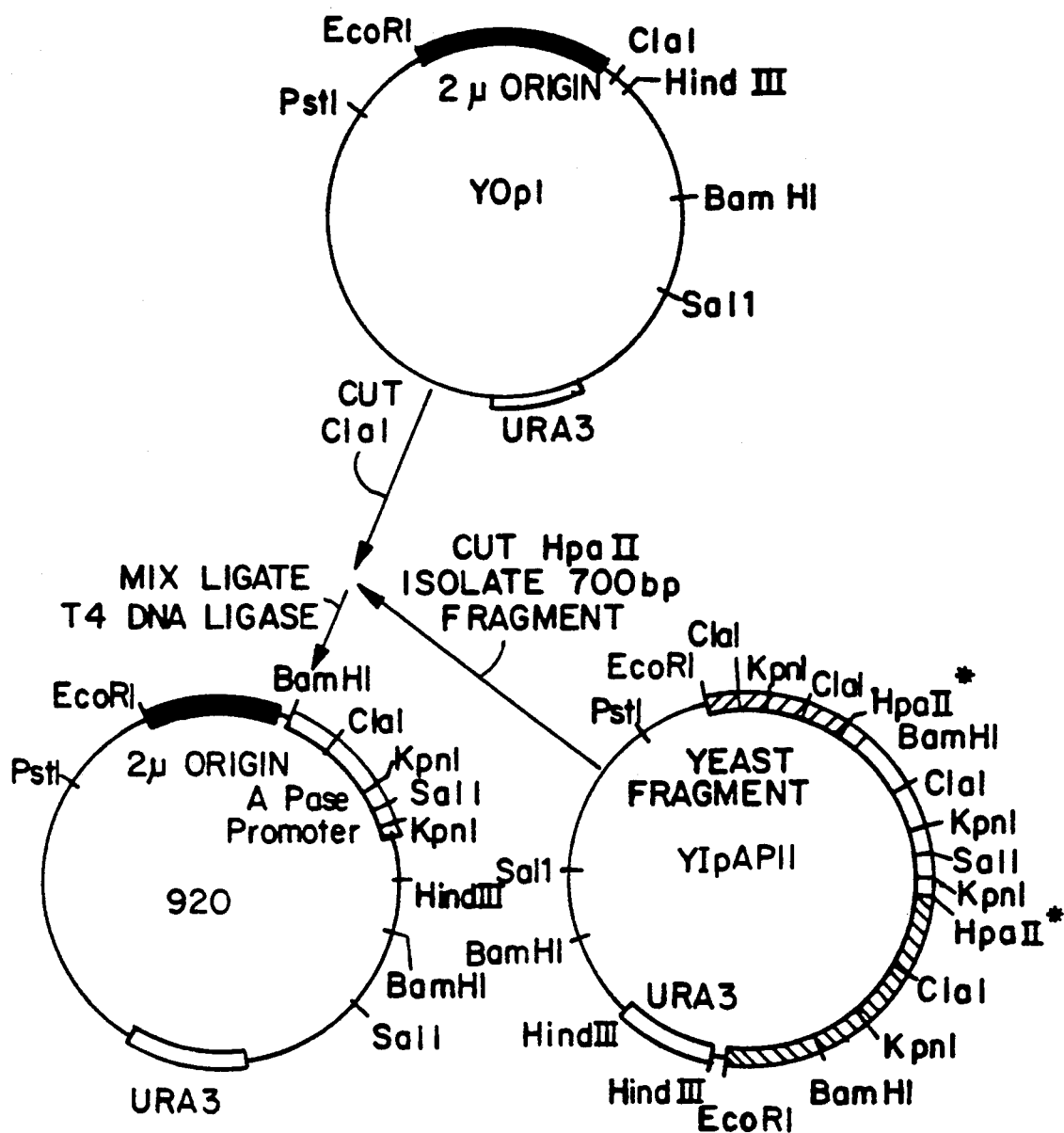
FIG. 18 illustrates the introduction of the yeast acid phosphatase promoter into the yeast expression vector.

Plasmid YIpAPII (Rogers et al., 1982, supra.) containing a full copy of the large subunit, P60 (PHO 5), of the acid phosphatase enzyme was mapped with various restrictions enzymes and HpaII was found to give a 700 bp restriction fragment containing 600 bp of upstream DNA sequence from the initiator (or start) codon for the structural gene whose position is known by reference to the ClaI site on the fragment (Thill et al., *Molecular Cell Biology* 3:5770–5779 (1983)). Plasmid YIpAPII was cut with HpaII and the DNA run on a preparative 1.5% agarose gel. The band of 700 bp, containing the promoter was electroeluted into a well cut into the gel as before and purified on a DEAE Sephacel column. The fragment was mixed with YOpl cut with ClaI and the DNA ligated with T4 DNA ligase. Since HpaII and ClaI have self complementary "sticky ends" these DNA's will ligate together. The ligation mix was transformed into HB101 and the ampicillin colonies screened for the presence of the promoter fragment. One such plasmid, 920, (See FIG. 18) was used for further constructions From the DNA sequence of the fragment of the acid phosphatase (PHO 5) gene FIG. 3 (Thill et al., 1983, supra.; Arima et al., *N.A.R.* 11:1657–1672 (1983), an area having four out of the six bases of a BglII restriction endonuclease recognition site was identified 5bp upstream from the initiator ATG. This area was used to create a BglII site at this point in the APase promoter sequence using a synthetic oligonucleotide linker of self complementary sequence CTAGCATGCTAG.

Figure 20:
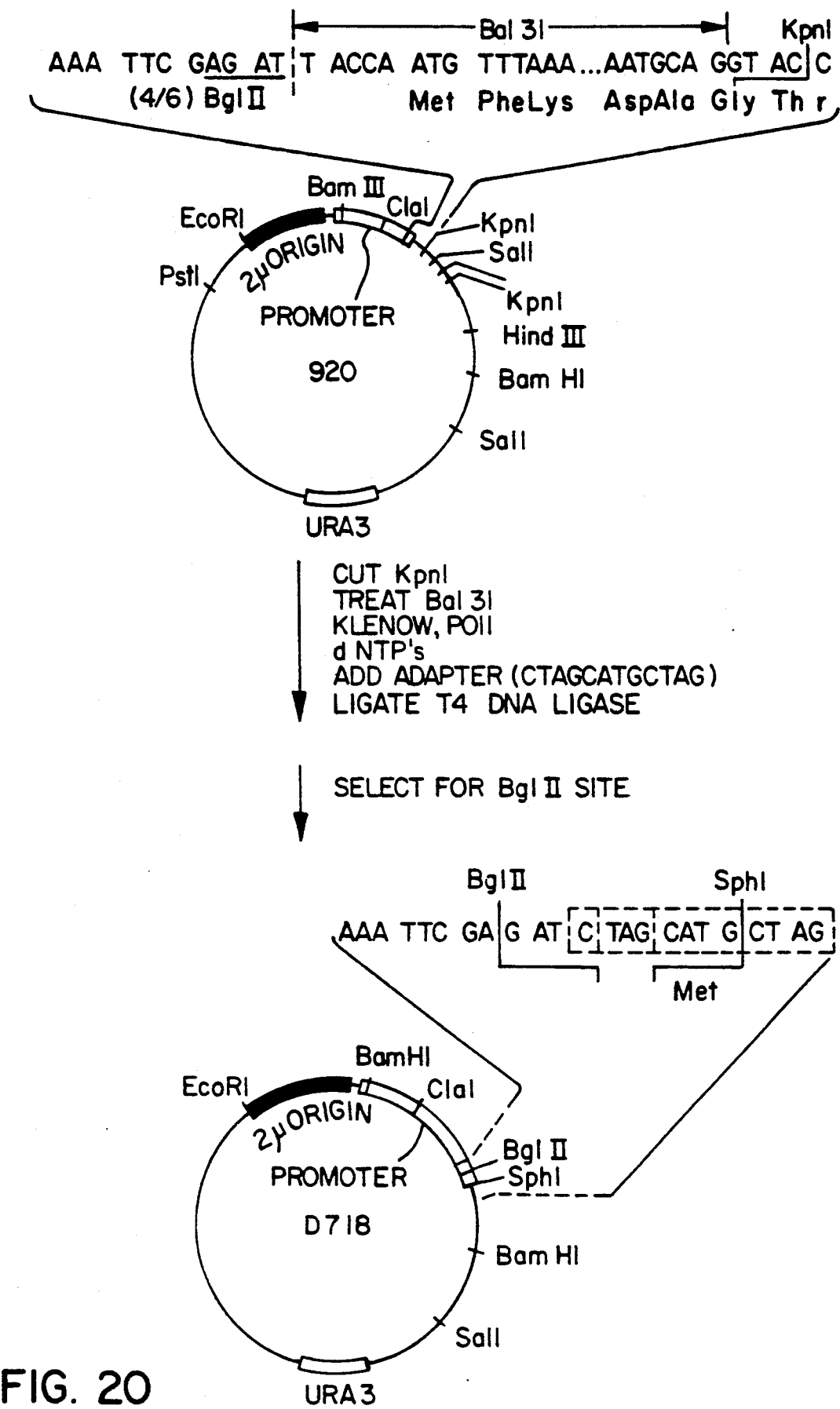
FIG. 20 illustrates the introduction of a unique BglII site at the 3' end of the acid phosphatase promoter

Plasmid 920 was cut with KpnI (see FIG. 20) and the DNA treated with the double strand exonuclease Ba131 (Legerski et al., *N.A.R.* 5:1145–1463 (1978)). At set time intervals, the reaction was stopped by the addition of ethylenediaminetetraacetic acid (EDTA) to 0.05M (Legerski et al., (1978) supra.). A portion of the plasmid from each time interval was digested with ClaI and run out on a 12% poly-acrylamide gel. The time point where the 300 bp ClaI/KpnI fragment had been digested to approximately 270 bp was noted. The remainder of the Ba131 treated plasmid from this point was treated with the Klenow fragment of DNA Polymerase I and the four dNTP's. A linker of self complementary sequence CTAGCATGCTAG was kinased, annealed and ligated to this plasmid DNA. The DNA was then circularized with T4 DNA ligase and transformed into HB101. Approximately two thousand ampicillin resistant colonies were washed from the plates and supercoiled plasmid DNA made from these *E. coli* cells (Maniatis et al., 1982, supra.). This pooled plasmid DNA was cut with the restriction enzyme BglII and the DNA run out on a preparative agarose gel. DNA running as a cut linear band was eluted into a well cut into the agarose and purified on a DEAE sephacel column. This purified DNA was re-circularized with T4 DNA ligase and transformed into HB101. Ampicillin resistant colonies were screened for the presence of a BglII site The only way for the plasmid to obtain a BglII site was for the site to be created at the junction of the Ba131 digested DNA and the linker. The only available sequence where this could occur within several hundred bp upstream of the KpnI site is 5b in front of the ATG initiation codon. One such plasmid containing a BglII site, D718 (FIG. 20) was checked and shown to be as expected by the dideoxynucleotide sequencing method of Sanger (Sanger et al., *Proc. Natl. Acad. Sci.* 74:5463–5467 (1977)).

Plasmid YlpAP11, has been deposited with the American Type Culture Collection in *E. coli* HB101 as follows

*E. coli* HB101 (YlpAP11)—ATCC No. 39570

Creation of a restriction site at the leader/native protein junction

From the sequence of acid phosphatase gene it can be seen (FIG. 18) that there is a KpnI site close to the start of the mature sequence. This has enabled us to introduce a restriction site at the junction of the leader sequence and the mature protein sequence using synthetic oligonucleotides of sequence

GCTCGAGGTAC

CGAGCTC

Figure 21A:
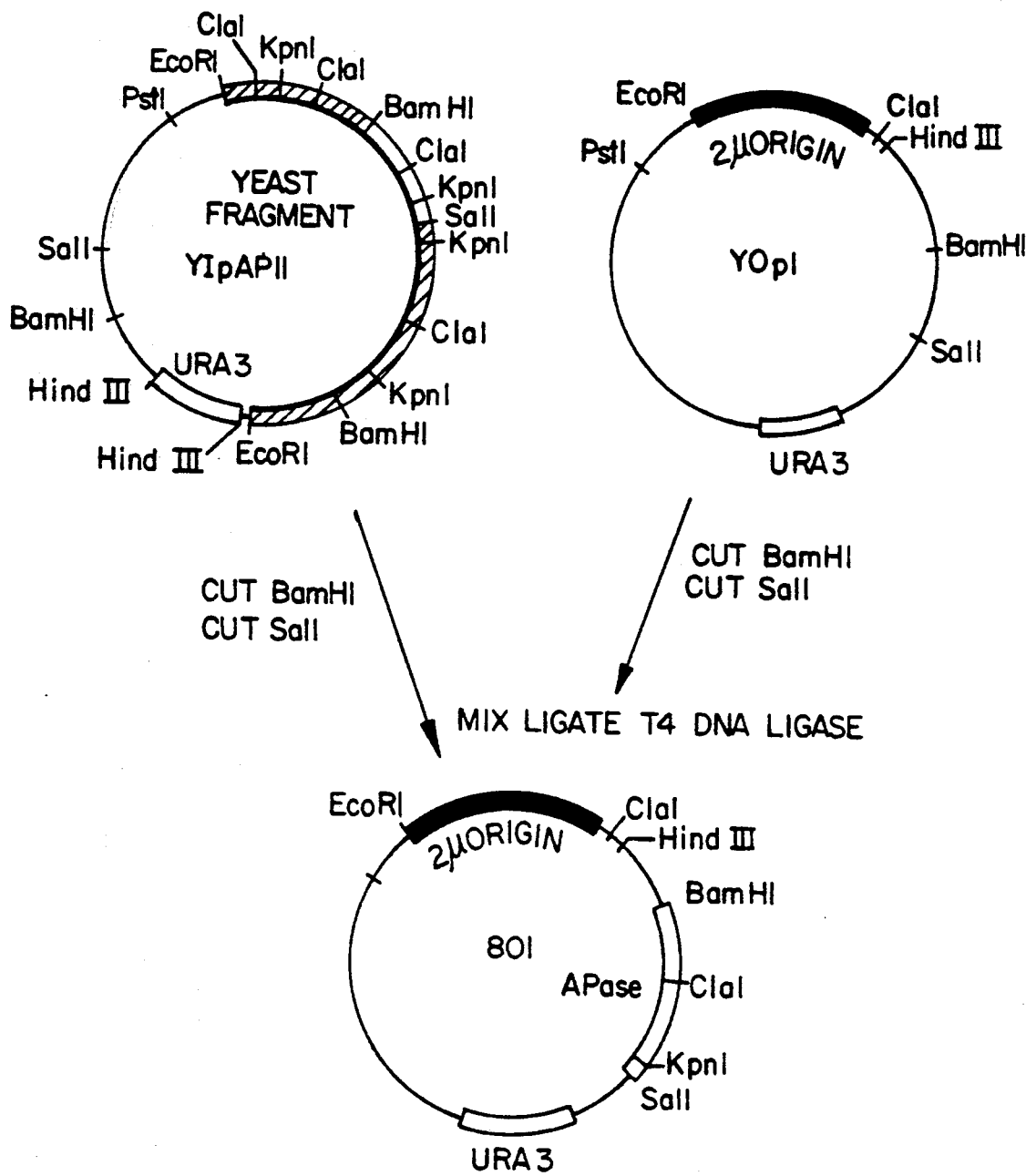
FIGS. 21A and 21B illustrate the introduction of a restriction site into the acid phosphatase gene for expression of the mature protein.
Figure 21B:
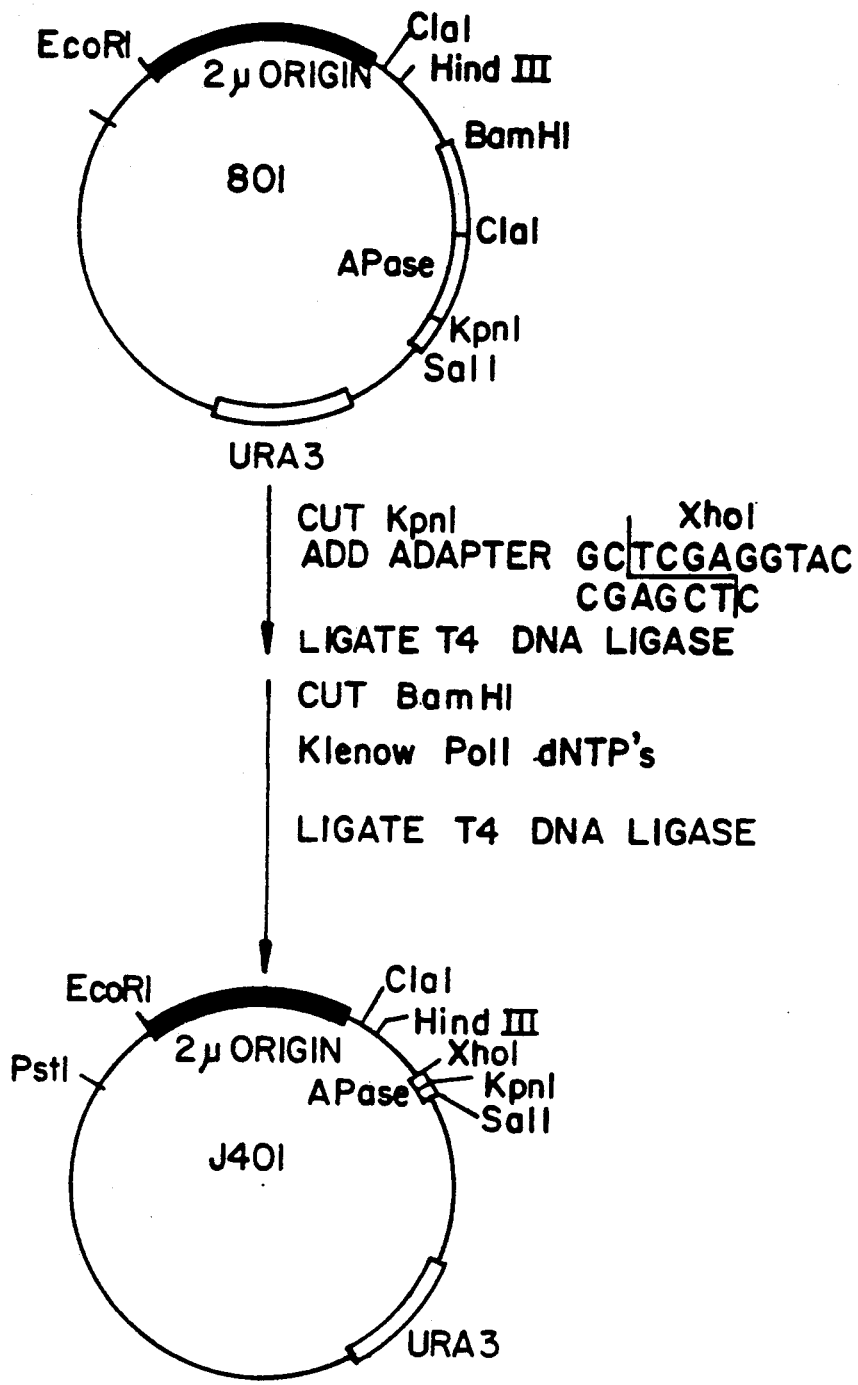

Since there are several KpnI sites in the acid phosphatase gene a fragment had to be subcloned from the 5' end of the gene. Plasmid YlpAP11 was cut with BamHI and SalI and the fragment containing the promoter subcloned into the BamHI/SalI sites of YOp1. (FIG. 21) Transformed bacteria were screened and plasmid 801 was found to have the correct sequence To introduce a restriction site at the 5' end of the mature sequence plasmid 801 was cut with KpnI and the adapter described above ligated to the KpnI site (FIG. 21). The plasmid was then cut with BamHI and the site "filled in" with the Klenow fragment of DNA polymerase I and the plasmid recircularized. Transformed bacterial colonies were screened for the presence of the adapter. One such plasmid (J401) was used for further constructions. As can be seen from FIG. 21 the adapter creates a XhoI site at the junction of the leader and mature acid phosphatase such that if the plasmid is cut with XhoI and the overhang digested with mung bean exonuclease there is a blunt site created at the correct position in the sequence at the start of the mature coding region.

Synthesis of a "leader less" clone of acid phosphatase

Figure 22A:
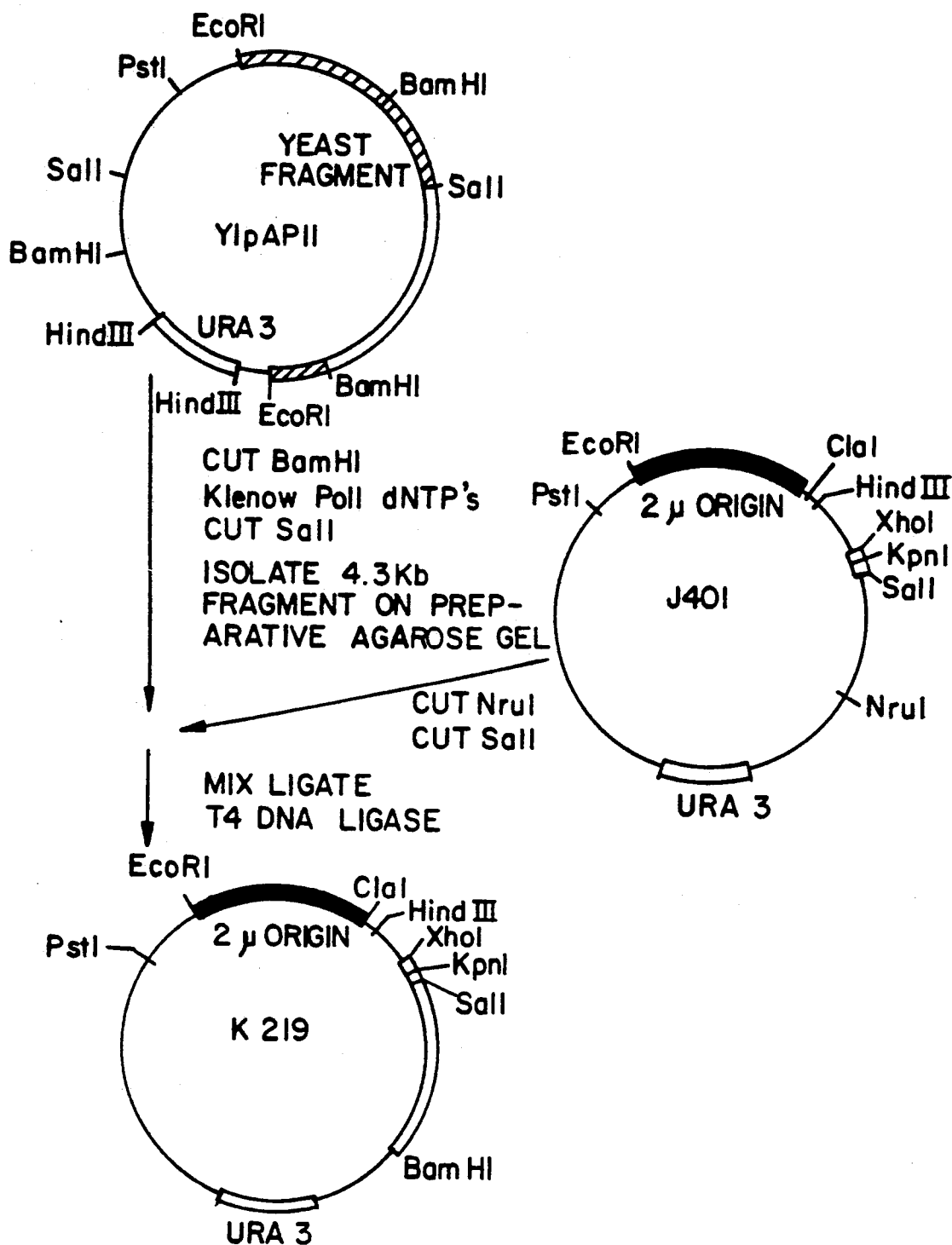
FIGS. 22A and 22B illustrate the synthesis of an expression vector which expresses the mature acid phosphatase gene from the acid phosphatase promoter.
Figure 22B:
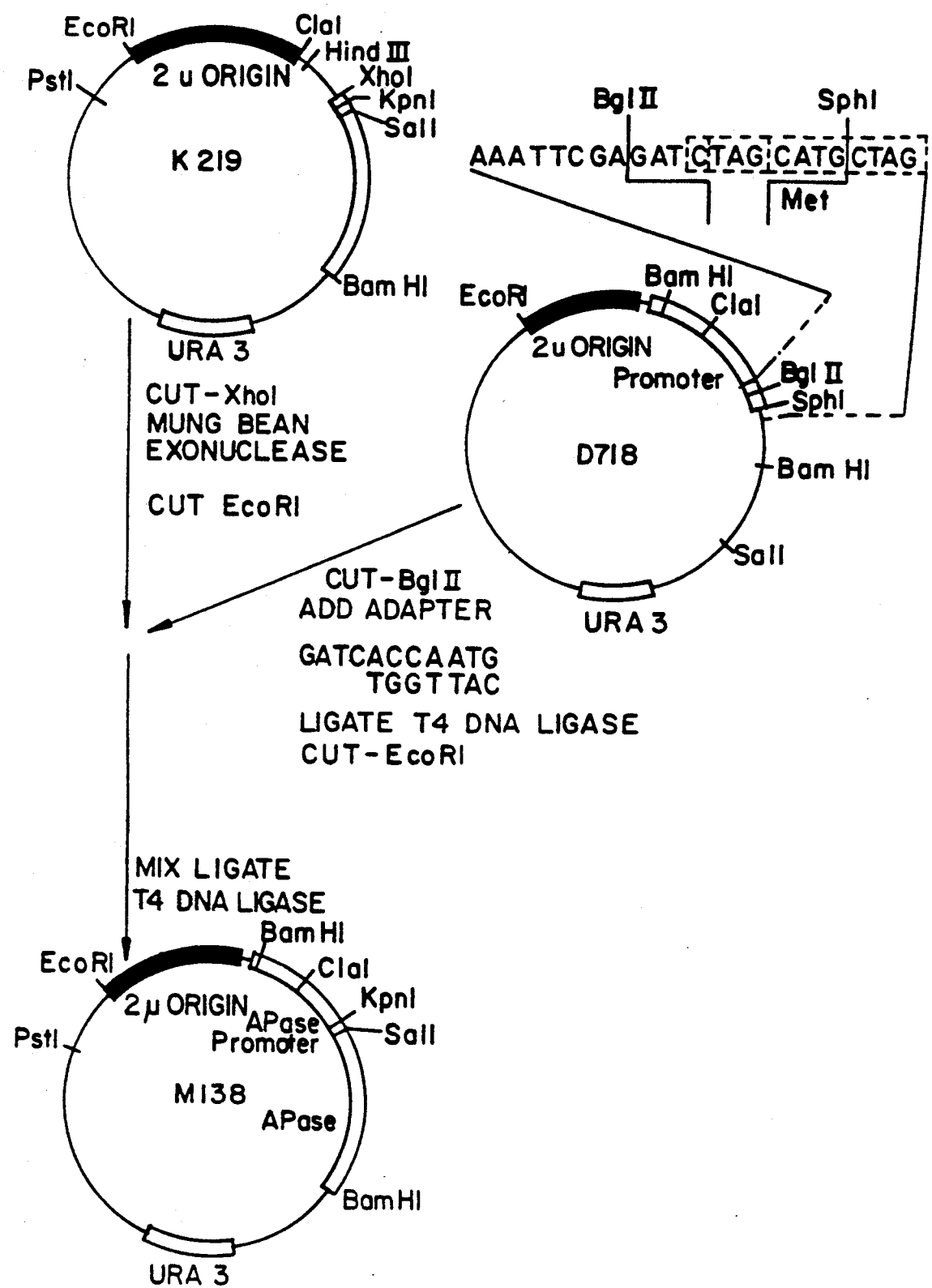

First the full length of acid phosphatase was constructed from plasmid J401. Plasmid YIpAP11 was cut with BamHI, the 5' overhang "filled in" with the Klenow fragment of DNA polymerase I and then cut with SalI and the BamHI/SalI fragment containing the APase gene purified by preparative gel electrophoresis. This fragment was then ligated into the SalI/NruI sites of plasmid J401 (FIG. 22). A "filled in" BamHI site ligated to an NruI site recreates the BamHI site Next the acid phosphatase promoter was reattached to the structural gene. Plasmid D718 was cut with BglII and an adapter of sequence

GATCACCAATG

TGGTTAC which recreates the acid phosphatase promoter sequence to the initiator methionine codon, ligated to the BglII site. The plasmid was then cut with EcoRI and the EcoRI to BglII adapter fragment (FIG. 22) cloned into plasmid K219 which had been cut with XhoI, treated with mung bean exonuclease to flush the ends of the DNA and then cut with EcoRI. Transformants were screened and plasmids containing the correct restriction fragments were sequenced and plasmids using the dideoxynucleotide sequencing method. Plasmid M138 was found to have the correct sequence at the junction of the promoter and the mature gene.

Addition of a yeast centromere to the Plasmid

The acid phosphatase promoter is inducible about 1,000 fold. The copy number of a yeast plasmid may be varied by using different origins of replication or a yeast centromere (Clark & Carbon, 1980; Tschumper & Carbon, 1983). A yeast centromere lowers the copy number of a 2u origin plasmid to about one copy per cell.

Figure 23:
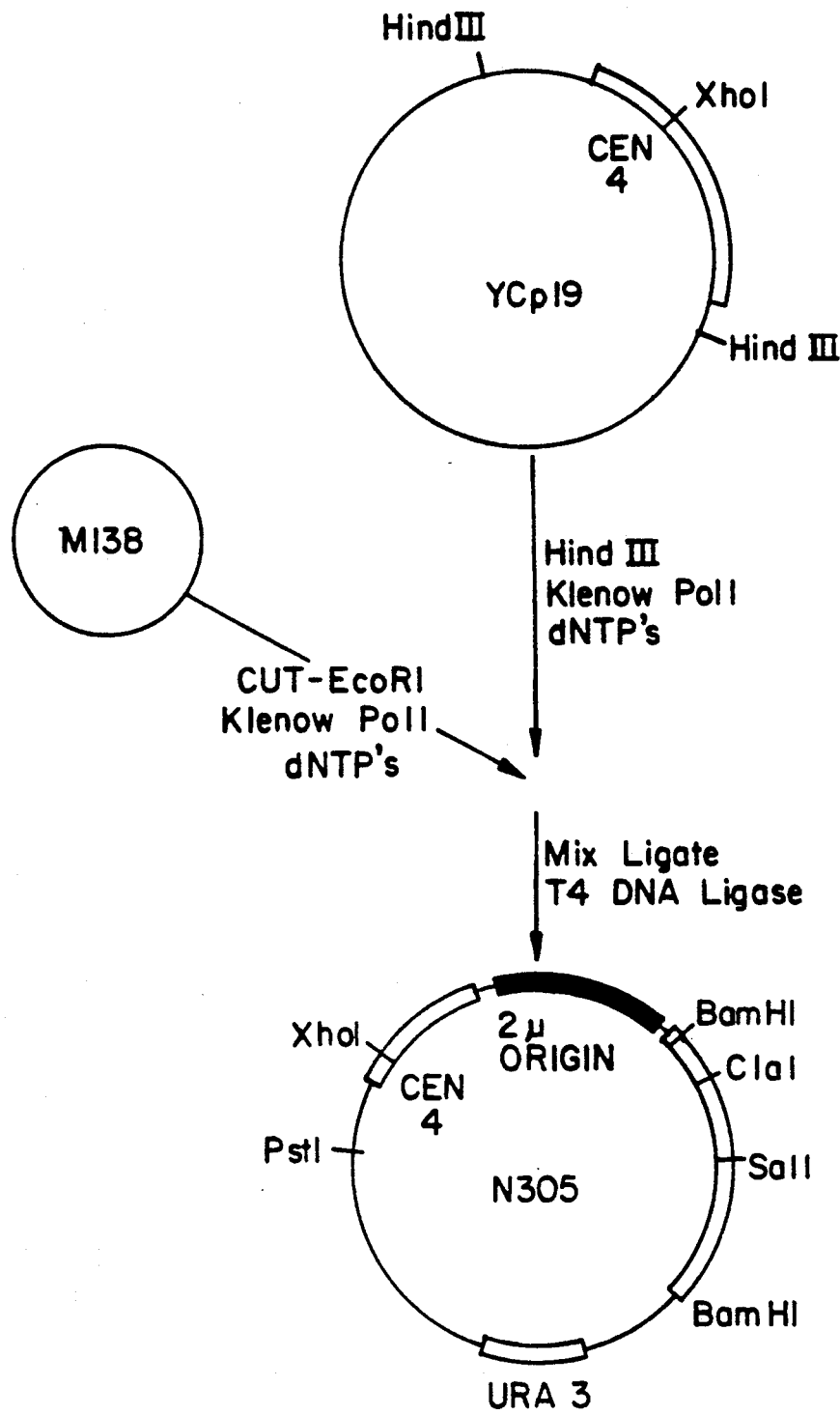
FIG. 23 illustrates the introduction of a yeast centromere into the plasmid containing the modified acid phosphatase gene.

Plasmid M138 was cut with EcoRI and the ends blunted with the Klenow fragment of DNA polymerase I. Next, plasmid YCP19 (FIG. 23), which contains the centromere from chromosome 4 of yeast (Parent et al., supra.), was cut with HindIII and the ends blunted with the Klenow fragment of DNA polymerase I. The fragment containing the centromere was then ligated into the EcoRI site of M138 to produce plasmid N305 (FIG. 22).

Expression of cytoplasmic acid phosphatase

Plasmids M138 and N305 were transformed into yeast together with a control plasmid M721. Uracil prototrophs were selected and grown in high phosphate MO media containing an excess of glucose (4%), in a one liter New Brunswick Scientific model F-200 fermenter. During growth, cell density was measured using a Bausch and Lomb Model Spectronic 20 at 600 nm. The results are set forth in Tables 1 and 2 below.

The fermenter was run at 30° C. and an agitation setting of 4. Nitrogen was continuously bubbled through the vessel at a rate of 430 cc/min and the off gas passed through a moisture trap of Dry-Rite and into a Perkin Elmer Mass Spectrometer gas analyzer to measure $CO_2$.

TABLE 2

CARBON DIOXIDE EVOLUTION IN UNINDUCED CULTURES

| Time Minutes | Cell Number ($\times 10^6$) | % Carbon Dioxide |
|---|---|---|
| CONTROL PLASMID M721 | | |
| 0 | 0.25 | 0.08 |
| 80 | 0.64 | 0.21 |
| 150 | 0.90 | 0.16 |
| 215 | 1.35 | 0.19 |
| 280 | 1.8 | 0.26 |
| 340 | 2.3 | 0.34 |
| 405 | 3.3 | 0.45 |
| 470 | 4.75 | 0.61 |
| 520 | 6.25 | 0.73 |
| 580 | 7.0 | 0.79 |
| 630 | 8.5 | 0.85 |
| 690 | 10.0 | 0.85 |
| 710 | 11.0 | 0.75 |
| PLASMID N305 | | |
| 0 | 1.1 | 0.17 |
| 60 | 1.35 | 0.22 |
| 108 | 1.5 | 0.26 |
| 165 | 2.0 | 0.35 |
| 245 | 3.0 | 0.50 |
| 345 | 5.0 | 0.76 |
| 390 | 6.5 | 0.92 |
| 465 | 8.5 | 1.05 |
| 520 | 10.0 | 1.15 |
| 610 | 14.5 | 1.02 |
| 685 | 16.0 | 0.86 |
| PLASMID M138 | | |
| 0 | 2.7 | 0.72 |
| 48 | 3.5 | 0.77 |
| 77 | 4.0 | 0.87 |
| 107 | 5.0 | 1.02 |
| 165 | 7.2 | 1.31 |
| 200 | 8.0 | 1.56 |
| 238 | 8.5 | 1.70 |
| 286 | 10.5 | 1.75 |
| 363 | 13.0 | 1.75 |
| 450 | 16.5 | 1.65 |
| 568 | 20.0 | 1.60 |
| 632 | 21.0 | 1.44 |

The level of carbon dioxide produced by the strains carrying the three different plasmids during growth on high phosphate media was found to vary (Table 2). The basal level of promoter activity in high phosphate media is sufficient to produce an effect on the rate of glycolysis. When the data was compiled and normalized for the same stage in the growth cycle, it was noted that the level of carbon dioxide produced by cultures growing in high phosphate media increased with the copy number of the plasmid. The strain carrying the multicopy plasmid produced twice as much carbon dioxide as the control and the strain carrying the single copy plasmid produced an intermediate level. Thus, the level of acid phosphatase can be controlled thereby controlling the level of cytoplasmic ATP in accord with this invention and increasing the rate of production of carbon dioxide.

EXAMPLE 3

The 2 micron plasmid of yeast has been shown to undergo site specific recombination between two inverted repeats (Hartley and Donelson, (1980) *Nature* 286:860–864). This recombination is catalysed by a specific recombinase (FLP), whose gene is located on the 2 Micron plasmid (Brbach and Hicks (1980) *Cell* 21:501–508). The GalI promoter is suppressed by glucose and induced by galactose (Yocum et al. (1984) *Mol. Cell Biol* 4:1985–1998). Thus if the GalI promoter were used to regulate FLP expression in the baking yeast, providing the natural 2 micron plasmid had been lost, the FLP gene will not be expressed until galactose is present. A growth fermenter is normally run under glucose limitation to prevent the Crabtree effect and the formation of ethanol and to maximize the production of cells. We have found that the GalI promoter is not glucose reprassed under these conditions. Addition of galactose to the fermenter thus induces the GalI promoter with the consequent expression of the FLP gene. Curing the 2 Micron plasmid of yeast may be accomplished using, for example, the method of Erhart and Hollenberg, *J.Bact.* 156:625–635. The FLP gene could also be expressed by another regulatable promoter as described above.

A clone of the FLP gene was therefore isolated and expressed from the regulated GalI promoter. To this end, the 2 micron plasmid of yeast was digested with XbaI and then digested with HindIII and a 1,450 bp XbaI/HindIII fragment isolated by preparative gel electrophoresis. The isolated fragment was then inserted into a conventional yeast plasmid containing the GalI promoter at the PvuII/SphI sites such that the FLP fragment was expressed from the GalI promoter to produce plasmid AR900 (FIG. 1). This allowed expression of the FLP gene protein from the GalI promoter.

Figure 2:
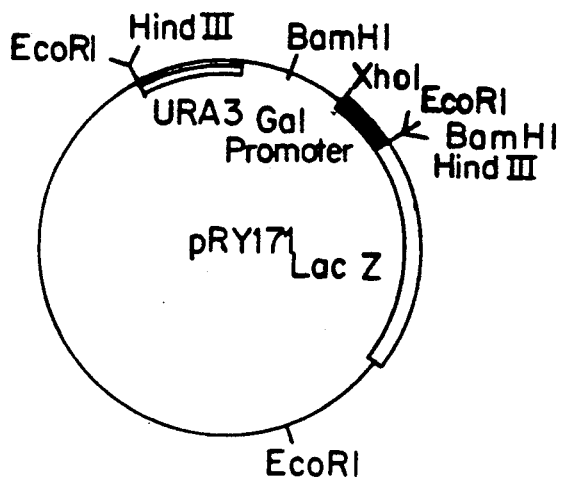
FIG. 2 illustrates a yeast plasmid containing the Gal promoter fused by the beta-gal coding region from E. coli.

Regulation of the GalI promoter during continuous growth under glucose limitation To test further the GalI promoter as a mechanism for regulating the FLP gene, a plasmid (PRY171 FIG. 2) containing the Gal promoter fused to the β-galactosidase coding region from *E. coli* (Parent et al. supra.), was transformed by integration into the genome of a laboratory yeast strain, e.g., KY114. This strain was inoculated into a chemostat where the culture was grown under glucose limitation in yeast minimal media. The culture was stabilized by growth, with a doubling time of 3.5 hours, for 48 hours. Galactose was coded to the fermenter at 2% final concentration and samples taken at regular intervals. β-galactosidase activity and protein concentration were measured using standard techniques (Miller 1972 Experiments in Molecular Genetics Cold Spring Harbor Laboratory, Cold Spring Harbor, NY; Rose et al., 1981 *Proc. Natl. Acad Sci.* 78:2460–2464). As can be seen (FIG. 3) the GalI promoter induced beta-galactosidase activity under conditions of glucose-limited growth when galactose was present.

To test the feasibility of using this galactose inducible FLP gene to regulate recombination, a strain of yeast lacking endogenous 2 micron plasmid and which had been previously transformed by integration with a plasmid containing a heterologous gene flanked by tandem repeats from the 2 micron plasmid of yeast (Hartley and Donelson 1980 *Nature* 286:860–864; Senecoff et al. 1985 *Proc. Natl. Acad. Sci. USA* 82:7270–7274; Andrews et al. (1985) *Cell* 40:795–803) was transformed with a plasmid containing the Gal/FLP fusion gene.

Figure 5A:
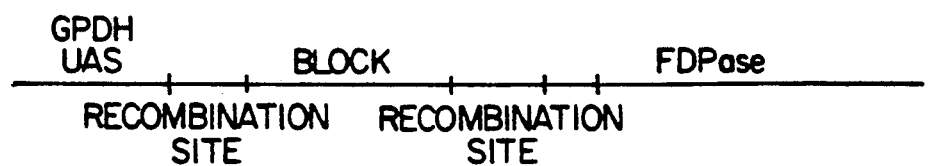
FIGS. 5A and 5B illustrate the loss of a transcriptional block from the GPDH promoter expressing the yeast FDPase gene.
Figure 5B:
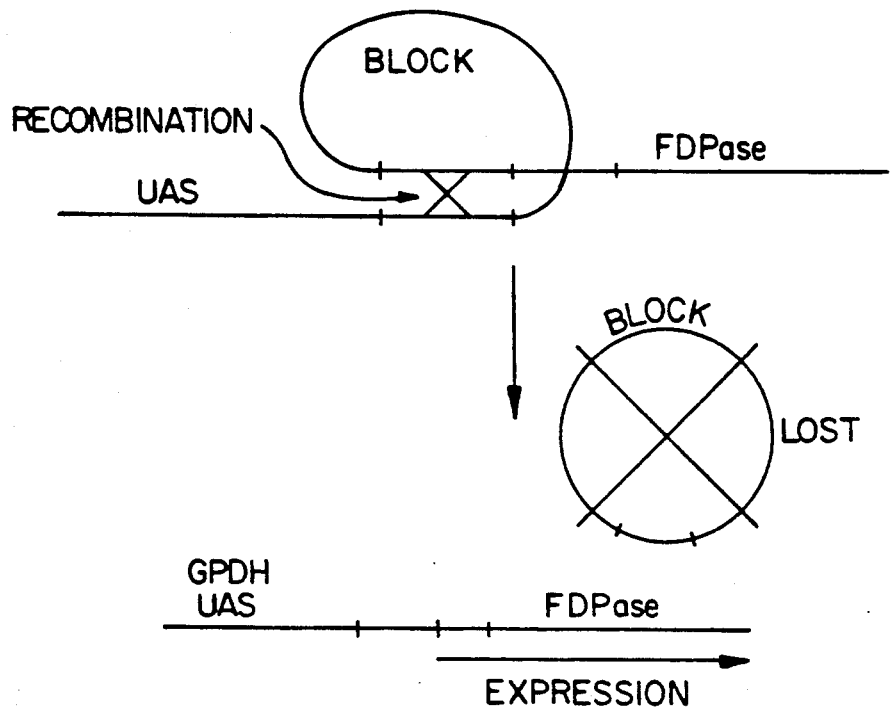

If the Gal/FLP fusion works, the strain should express the heterologous gene when growing on glucose (which suppresses the GalI promoter). When the strain is grown on galactose, however, the heterologous gene should be excised from the genome by recombination resulting in loss of the gene (FIG. 4). This was indeed found to be the case since on glucose media 97% of the colonies expressed the heterologous gene while on galactose media 0% of the colonies contained the heterologous gene activity Next an expression block, e.g., a DNA sequence containing a transcriptional block such as the URA3 HindIII fragment, or a silencer region or a transcription terminator (Brand et al., 1985, *Cell* 21:501–508), is inserted into the promoter, e.g., the GPDH promoter, between the upstream activation sequence and the translational start site This transcriptional block element is flanked by DNA sequences (inserted as synthetic oligonucleotides, illustrated in Table 1) shown to be recognized by the FLP gene product as substrates for site-specific recombination (Senecoff et al. supra.; Andrews et al. supra.). Thus regulation operates by addition of galactose to a growing nonglucose-repressed culture of yeast. Galactose induces the synthesis of the FLP protein which catalyzes a recombination dent between the DNA sequences flanking the expression block. The recombination event removes the expression block, thereby allowing expression of the heterologous gene, e.g., the gene for FLPase from the GPDH promoter. FIG. 5.

Figure 6:
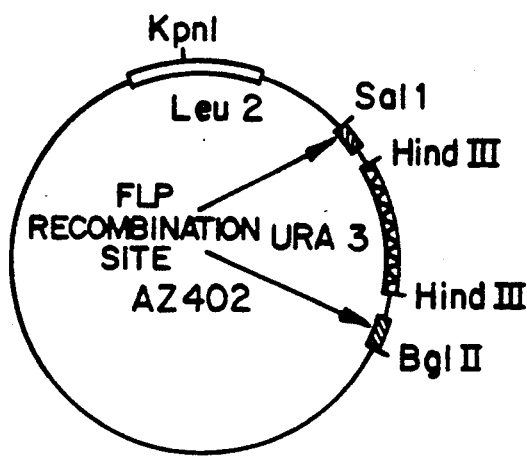
FIG. 6 illustrates a plasmid containing an expression block bounded by SalI/BglII restriction sites.

Such a block surrounded by recombination sites illustrated in FIG. 6 has been deposited and can be inserted into the promoter of choice by those skilled in the art by first inserting a BglII/SalI linker into the promoter sequence, at a site which allows expression, using site directed mutagenesis as described (Zoller and Smith *N.A.R.* 10:6487–6500 (1982); *Methods Enzymol.* 100:468–500 (1983), *DNA* 3:479–488 (1984), and then inserting the transcriptional block from plasmid AZ402 a a BglII/SalI fragment.

TABLE 1

| Sequence for FLP Catalysed Site Specific Recombination Site |
|---|
| TCGACGCTTTGAAGTTCCTATTCCGAAGTTCCTA |
| GCGAAACTTCAAGGATAAGGCTTCAAGGAT (cont'd on next line) |
| TTCTCTAGAAAGTATAGGAACTTCAGAGCGCTTA |
| AAGAGATCTTTCATATCCTTGAAGTCTCGCGAATCTAG |

This FLP expression system can be used to regulate the expression of virtually any gene in a variety of host cells. Generally, the regulated expression in a host cell of a heterologous DNA sequence may be effected using a two vector system. The first vector contains a DNA sequence encoding a FLP protein (FLP DNA) operatively linked to a regulatable promoter. An example of such a vector is AR900 which contains the FLP gene operatively linked to the GalI promoter. Similar vectors containing other promotersmay be constructed by routine methods by excising the GalI promoter from AR900 with EcoRI and SphI and substituting therefor any desired promoter, again using conventional techniques and appropriate linkers, if necessary. The second vector contains the heterologous DNA sequence to be expressed, operatively linked to a promoter which contains, inserted therein, an expression block flanked by DNA sequences (flanking DNA) which are recognized by FLP protein. Such vectors may be constructed by conventional means using the SalI-BglII cassette from AZ402 together with readily available and/or synthesized components. The SalI-BglII cassette from AZ402 contains the URA3 expression block as a HindIII fragment flanked by FLP-recognized recombination sites. Other expression blocks may be substituted for URA3 using conventional methods, and again, conventional linkers, if necessary. The expression block, e.g., the SalI-BglII cassette from AZ402, is then inserted, with conventional linkers if necessary, into the promoter region of a vector containing the heterologous DNA sequence operatively linked to a promoter such that expression is blocked. Suitable insertion may be readily confirmed empirically by observation of the phenotype of cells transformed with the vector and/or by monitoring the culture medium for the absence of the expression system wherein the FLP protein produced by expression of the FLP DNA in the first vector catalyzes a recombination between the flanking DNA of the second vector, thereby removing the expression block and allowing expression of the heterologous DNA sequence. Naturally, when using any specific host cell, the vectors should contain any genetics elements required by the particular host, as is well known in the art.

Using the above-described vectors and regulated promoters we have produced yeast strains characterized by higher rates of $CO_2$ production, and have produced such strains by introducing into the host strain (i) an ATP-consuming futile cycle and, in another embodiment of the invention, (ii) enhanced cytoplasmic ATPase activity.

What is claimed is:

1. A process for increasing the rate of carbon dioxide and ethanol production of yeast of the genus Saccharomyces which comprises:
   (a) transforming said yeast with DNA encoding the yeast enzyme fructose-1,6-diphosphatase, said DNA being under the control of a regulatable Saccharomyces yeast promoter, wherein the promoter is selected from the group consisting of genes in galactose, maltose, phosphate, nitrogen metabolism, isocytochrome and alcohol dehydrogenase II promoters; and
   (b) inducing the expression of the DNA during growth on glucose by activating the regulatable promoter.

2. The process according to claim 1, wherein the DNA encoding fructose-1,6-diphosphatase is mutagenzied such that codon 12 of the mutagenized DNA encodes alanine, threonine, valine, or cysteine.

3. The process in accordance with claim 1, wherein the regulatable promoter is a temperature sensitive promoter such that the fructose-1,6-diphosphatase is expressed only at a predetermined temperature.

4. The process in accordance with claim 1, wherein the regulatable promoter permits constitutive expression of the DNA.

5. A process for increasing the rate of carbon dioxide and ethanol production of yeast of the genus Saccharomyces which comprises:
   (a) genetically modifying a yeast DNA encoding an exocellular acid phosphatase, said genetic modification causing acid phosphatase to remain with the yeast cytoplasm and to catalyze the controlled hydrolysis of intracellular ATP;
   (b) inserting the genetically modified DNA into a cell; and
   (c) growing said yeast in suitable culture conditions.

6. A process for increasing the rate of carbon dioxide and ethanol production of yeast of the genus Saccharomyces which comprises:
   (a) genetically modifying a yeast DNA encoding an exocellular acid phosphatase, said genetic modification causing acid phosphatase to remain within the yeast cytoplasm and to catalyze the controlled hydrolysis of intracellular ATP;
   (b) inserting the genetically modified DNA into a cell; and
   (c) growing said yeast in suitable culture conditions, wherein the genetic modification comprises deletion of a functional secretory leader sequence from said DNA.

7. The process of claim 6, wherein the DNA is contained in a vector comprising an autonomously replicating single copy, centromere containing plasmid.

8. The process of claim 6, wherein the DNA is contained in a vector comprising a multicopy plasmid containing the yeast $2\mu$ origin of replication.

9. The process of claim 6, wherein the DNA is inserted into the genome of the yeast.

10. A yeast cell of the genus Saccharomyces containing a DNA encoding yeast fructose-1,6-diphosphatase, said DNA being under the control of a regulatable Saccharomyces promoter and being capable of expression during growth on glucose by activation of the regulatable promoter, wherein said yeast cell is characterized by an increased rate of carbon dioxide and ethanol production.

11. The yeast cell of claim 10 wherein the regulatable promoter permits constitutive expression of the DNA.

* * * * *